(12) United States Patent
Lisanti et al.

(10) Patent No.: US 11,672,810 B2
(45) Date of Patent: Jun. 13, 2023

(54) THERAPEUTICS AND METHODS FOR PREDICTING AND OVERCOMING ENDOCRINE RESISTANCE IN BREAST CANCER

(71) Applicant: LUNELLA BIOTECH, INC., Ottawa (CA)

(72) Inventors: Michael P. Lisanti, Ottawa (CA); Federica Sotgia, Ottawa (CA)

(73) Assignee: LUNELLA BIOTECH, INC., Ontario (CA)

( * ) Notice: Subject to any disclaimer, the term of this patent is extended or adjusted under 35 U.S.C. 154(b) by 0 days.

(21) Appl. No.: 17/614,194

(22) PCT Filed: May 20, 2020

(86) PCT No.: PCT/US2020/033789
§ 371 (c)(1),
(2) Date: Nov. 24, 2021

(87) PCT Pub. No.: WO2020/242857
PCT Pub. Date: Dec. 3, 2020

(65) Prior Publication Data
US 2022/0202836 A1    Jun. 30, 2022

Related U.S. Application Data

(60) Provisional application No. 62/852,477, filed on May 24, 2019.

(51) Int. Cl.
| | |
|---|---|
| *A61K 31/65* | (2006.01) |
| *A61P 35/00* | (2006.01) |
| *A61K 31/122* | (2006.01) |
| *A61K 31/138* | (2006.01) |
| *A61K 31/165* | (2006.01) |
| *A61K 31/167* | (2006.01) |
| *A61K 31/36* | (2006.01) |
| *A61K 31/375* | (2006.01) |
| *A61K 31/4375* | (2006.01) |
| *A61K 31/44* | (2006.01) |
| *A61K 31/47* | (2006.01) |
| *A61K 31/4706* | (2006.01) |
| *A61K 31/4745* | (2006.01) |
| *A61K 31/565* | (2006.01) |
| *A61K 31/7004* | (2006.01) |
| *A61K 31/7048* | (2006.01) |

(Continued)

(52) U.S. Cl.
CPC ............ *A61K 31/65* (2013.01); *A61K 31/122* (2013.01); *A61K 31/138* (2013.01); *A61K 31/165* (2013.01); *A61K 31/167* (2013.01); *A61K 31/36* (2013.01); *A61K 31/375* (2013.01); *A61K 31/4375* (2013.01); *A61K 31/44* (2013.01); *A61K 31/47* (2013.01); *A61K 31/4706* (2013.01); *A61K 31/4745* (2013.01); *A61K 31/565* (2013.01); *A61K 31/7004* (2013.01); *A61K 31/7048* (2013.01); *A61K 31/7052* (2013.01); *A61P 35/00* (2018.01); *G01N 33/6848* (2013.01); *G01N 33/6893* (2013.01); *G01N 2800/7028* (2013.01)

(58) Field of Classification Search
CPC .... A61K 31/65; A61K 31/122; A61K 31/138; A61K 31/165; A61K 31/167; A61K 31/36; A61K 31/375; A61K 31/4375; A61K 31/44; A61K 31/47; A61K 31/4706; A61K 31/4745; A61K 31/565; A61K 31/7004; A61K 31/7048; A61K 31/7052; A61P 35/00; G01N 33/6848; G01N 33/6893; G01N 2800/7028
USPC ......................................................... 514/29
See application file for complete search history.

(56) References Cited

U.S. PATENT DOCUMENTS

2014/0364595 A1 * 12/2014 Bapat ..................... A61K 8/347
544/370
2015/0079078 A1    3/2015 Umar et al.
(Continued)

FOREIGN PATENT DOCUMENTS

| WO | 2018/170109 | 9/2018 |
| WO | WO 2018/213764 | * 11/2018 |
| WO | 2019/075209 | 4/2019 |

OTHER PUBLICATIONS

Rajcevic et al. iTRAQ-based Proteomics Profiling Reveals Increased Metabolic Activity and Cellular Cross-talk in Angiogenic Compared with Invasive Glioblastoma Phenotype. Molecular & Cellular Proteomics 8:2595-2612, 2009. (Year: 2009).*

(Continued)

*Primary Examiner* — Yih-Horng Shiao
(74) *Attorney, Agent, or Firm* — Nixon & Vanderhye, P.C.

(57) ABSTRACT

MCF7-fibroblast co-cultures are a valuable model of resistance to apoptosis induced by hormonal therapies, such as Tamoxifen and Fulvestrant. These mixed co-cultures demonstrate the induction of mito-stemness and ribo-stemness features. Molecular therapeutic targets were identified through label-free proteomics of MCF7-fibroblast co-cultures, and independently validated using a bioinformatics approach. The resulting Mito-Signature is prognostic of endocrine treatment failure, tumor recurrence, and distant metastasis, and may be used to identify patients at risk of treatment failure. Such patients may be treated with a mitochondrial biogenesis inhibitor to reduce the risk of treatment failure, and/or to increase the effectiveness of the hormone therapy.

30 Claims, 17 Drawing Sheets

(51) Int. Cl.
*A61K 31/7052* (2006.01)
*G01N 33/68* (2006.01)

(56) References Cited

U.S. PATENT DOCUMENTS

2016/0265066 A1    9/2016   Croce et al.
2016/0266126 A1    9/2016   Shipitsin et al.

OTHER PUBLICATIONS

Peiris-Pagès et al. Mitochondrial and ribosomal biogenesis are new hallmarks of stemness, oncometabolism and biomass accumulation in cancer: Mito-stemness and ribo-stemness features. Aging 2019, vol. 11., pp. 1-35. (Year: 2019).*
Pucci et al. Carnitine palmitoyl transferase-1A (CPT1A): a new tumor specific target in human breast cancer. Oncotarget, vol. 7, No. 15, p. 19982-19996, Published: Jan. 21, 2016. (Year: 2016).*
International Search Report for PCT/US2020/033789 dated Jul. 29, 2020, 2 pages.
Written Opinion of the ISA for PCT/US2020/033789 dated Jul. 29, 2020, 4 pages.

* cited by examiner hTERT-BJ1-RFP

MCF7-GFP

Control

250 µM

500 µM 1 mM

THERAPEUTICS AND METHODS FOR PREDICTING AND OVERCOMING ENDOCRINE RESISTANCE IN BREAST CANCER

RELATED APPLICATIONS

This application is the U.S. national phase of International Application No. PCT/US2020/033789 filed May 20, 2020 which designated the U.S. and claims priority to U.S. Provisional Patent Application No. 62/852,477 filed May 24, 2019, the entire contents of each of which are hereby incorporated by reference.

FIELD

The present disclosure relates to therapeutics and methods for predicting and overcoming endocrine resistance in cancer, and in particular, breast cancer.

BACKGROUND

Researchers have struggled to develop new anti-cancer treatments. Conventional cancer therapies (e.g. irradiation, alkylating agents such as cyclophosphamide, and anti-metabolites such as 5-Fluorouracil) have attempted to selectively detect and eradicate fast-growing cancer cells by interfering with cellular mechanisms involved in cell growth and DNA replication. Other cancer therapies have used immunotherapies that selectively bind mutant tumor antigens on fast-growing cancer cells (e.g., monoclonal antibodies). Unfortunately, tumors often recur following these therapies at the same or different site(s), indicating that not all cancer cells have been eradicated. Relapse may be due to insufficient chemotherapeutic dosage and/or emergence of cancer clones resistant to therapy. Hence, novel cancer treatment strategies are needed.

Advances in mutational analysis have allowed in-depth study of the genetic mutations that occur during cancer development. Despite having knowledge of the genomic landscape, modern oncology has had difficulty with identifying primary driver mutations across cancer subtypes. The harsh reality appears to be that each patient's tumor is unique, and a single tumor may contain multiple divergent clone cells. What is needed, then, is a new approach that emphasizes commonalities between different cancer types. Targeting the metabolic differences between tumor and normal cells holds promise as a novel cancer treatment strategy. An analysis of transcriptional profiling data from human breast cancer samples revealed more than 95 elevated mRNA transcripts associated with mitochondrial biogenesis and/or mitochondrial translation. Additionally, more than 35 of the 95 upregulated mRNAs encode mitochondrial ribosomal proteins (MRPs). Proteomic analysis of human breast cancer stem cells likewise revealed the significant overexpression of several mitoribosomal proteins as well as other proteins associated with mitochondrial biogenesis.

Mitochondria are extremely dynamic organelles in constant division, elongation and connection to each other to form tubular networks or fragmented granules in order to satisfy the requirements of the cell and adapt to the cellular microenvironment. The balance of mitochondrial fusion and fission dictates the morphology, abundance, function and spatial distribution of mitochondria, therefore influencing a plethora of mitochondrial-dependent vital biological processes such as ATP production, mitophagy, apoptosis, and calcium homeostasis. In turn, mitochondrial dynamics can be regulated by mitochondrial metabolism, respiration and oxidative stress. Thus, it is not surprising that an imbalance of fission and fusion activities has a negative impact on several pathological conditions, including cancer. Cancer cells often exhibit fragmented mitochondria, and enhanced fission or reduced fusion is often associated with cancer, although a comprehensive mechanistic understanding on how mitochondrial dynamics affects tumorigenesis is still needed.

Cancer stem cells (CSCs) are now thought to be one of the major drivers behind treatment failure in many cancer types, including breast cancer. As a consequence, residual CSCs, which are chemo-resistant and radio-resistant, result in tumor recurrence and distant metastasis, ultimately killing most cancer patients. Therefore, there is an urgent need to identify and understand the metabolic weak points within CSCs, to drive new drug discovery and therapies, ultimately for patient benefit. This requires new innovative approaches towards understanding "stemness" features and identifying specific metabolic targets in CSCs.

An objective of this disclosure is to identify and describe a method for developing biomarker signatures prognostic of cancer treatment failure, including tumor recurrence, metastasis, and/or hormone therapy resistance. Another object of this disclosure is to describe methods for identifying patients at risk of cancer treatment failure, and candidates for treatment with mitochondrial biogenesis inhibitors to reduce the risk of treatment failure, and/or increase the effectiveness of hormone therapy.

SUMMARY

In order to identify new characteristic features of "stemness" in cancer cells, the proteomic profiles of 3D-spheroid cultures of MCF7 breast cancer cells have been compared with MCF7 monolayer cells, processed in parallel. These 3D-spheroids were grown under anchorage-independent conditions and are also known as mammosphere cultures, which are highly enriched in CSCs and cancer progenitor cells. Using this approach, the inventors previously demonstrated that under these 3D growth conditions, MCF7 cells up-regulated the expression of >60 mitochondrial-related proteins and >80 proteins related to protein synthesis, including ribosomal biogenesis. Moreover, pharmacologically targeting protein synthesis and/or mitochondrial function are shown to be sufficient to eradicate CSCs.

This description refers to these characteristic proteomic changes as "mito-stemness" and "ribo-stemness," characteristics associated with CSCs. These stemness features are also similarly up-regulated during the co-culture of MCF7 breast cancer cells with fibroblasts. As described herein, MCF7-fibroblast co-cultures increase their biosynthetic cellular machinery, to expand their capacity to increase biomass. Therefore, "mito-stemness" and "ribo-stemness" features are actually oncogenic hallmarks of the ability and readiness of cancer cells to aggressively undergo biomass accumulation.

The implications of these oncogenic hallmarks allow for detecting and treating Tamoxifen-resistance. The MCF7-fibroblast co-culture system has been validated as a bonafide model of Tamoxifen-resistance, which includes a stromal microenvironment, making it perhaps more physiologically-relevant.

Described herein are methods for developing biomarker signatures prognostic of cancer treatment failure, including tumor recurrence, metastasis, and/or hormone therapy resistance. Also described are methods for identifying patients at risk of cancer treatment failure, and candidates for treatment with mitochondrial biogenesis inhibitors to reduce the risk of treatment failure, and/or increase the effectiveness of hormone therapy.

Some embodiments may be methods for identifying and treating endocrine therapy resistance in a cancer. A biological epithelial sample of the cancer may be obtained, and the level of each biomarker in a Mito-Signature comprising HSPD1, VDAC2, and CPT1A, in the biological sample may be determined. The determined level is compared to a threshold level for each biomarker in the Mito-Signature, and a pharmaceutically effective amount of a mitochondrial biogenesis inhibitor is administered if the determined levels of at least two of the biomarkers in the Mito-Signature exceeds the threshold level. Preferably, the mitochondrial biogenesis inhibitor is administered if the determined level for all three biomarkers exceeds the threshold level. The threshold level for each biomarker in the Mito-Signature may be determined using a non-cancerous epithelial sample from the same subject. The cancer comprises breast cancer.

The mitochondrial biogenesis inhibitor may be selected from numerous available inhibitor compounds. The available inhibitor compounds include doxycycline, azithromycin, myristoyl derivatives of 9-amino-doxycycline, such as compounds having the general formula:

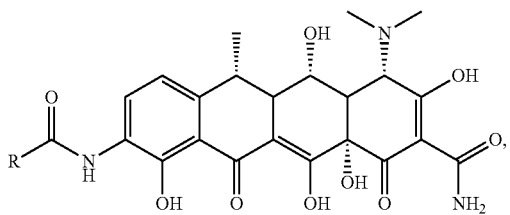

wherein R comprises a C4-C18 alkyl, or a pharmaceutically acceptable salt thereof. The mitochondrial biogenesis inhibitor may be a mitoriboscin, a combination of an oxidative metabolism inhibitor and a glycolytic metabolism inhibitor, a repurposcin, an antimitoscin, a mitoketoscin, a mitoflavoscin, a mitoflavin, a TPP-derivative, or an MDIVI-1 derivative. These and other inhibitor compounds are described more fully below, and in the applications incorporated by reference.

Some embodiments may be methods for increasing the effectiveness of an endocrine therapy on breast cancer. The 3-gene Mito-Signature may be used to identify patients at risk of endocrine therapy resistance, through elevated levels of the biomarkers in the Mito-Signature relative to a threshold level, and a pharmaceutically effective amount of a mitochondrial biogenesis inhibitor may be administered to such patients. The endocrine therapy may be, for example, Tamoxifen and Fulvestrant. In some embodiments, the mitochondrial biogenesis inhibitor may be administered before administering the endocrine therapy. In some embodiments, the mitochondrial biogenesis inhibitor may be administered at the same time as administering the endocrine therapy.

These and other embodiments will be apparent to the person having an ordinary level of skill in the art in view of this description, the claims appended hereto, and the applications incorporated by reference herein.

DESCRIPTION

Figure 1:
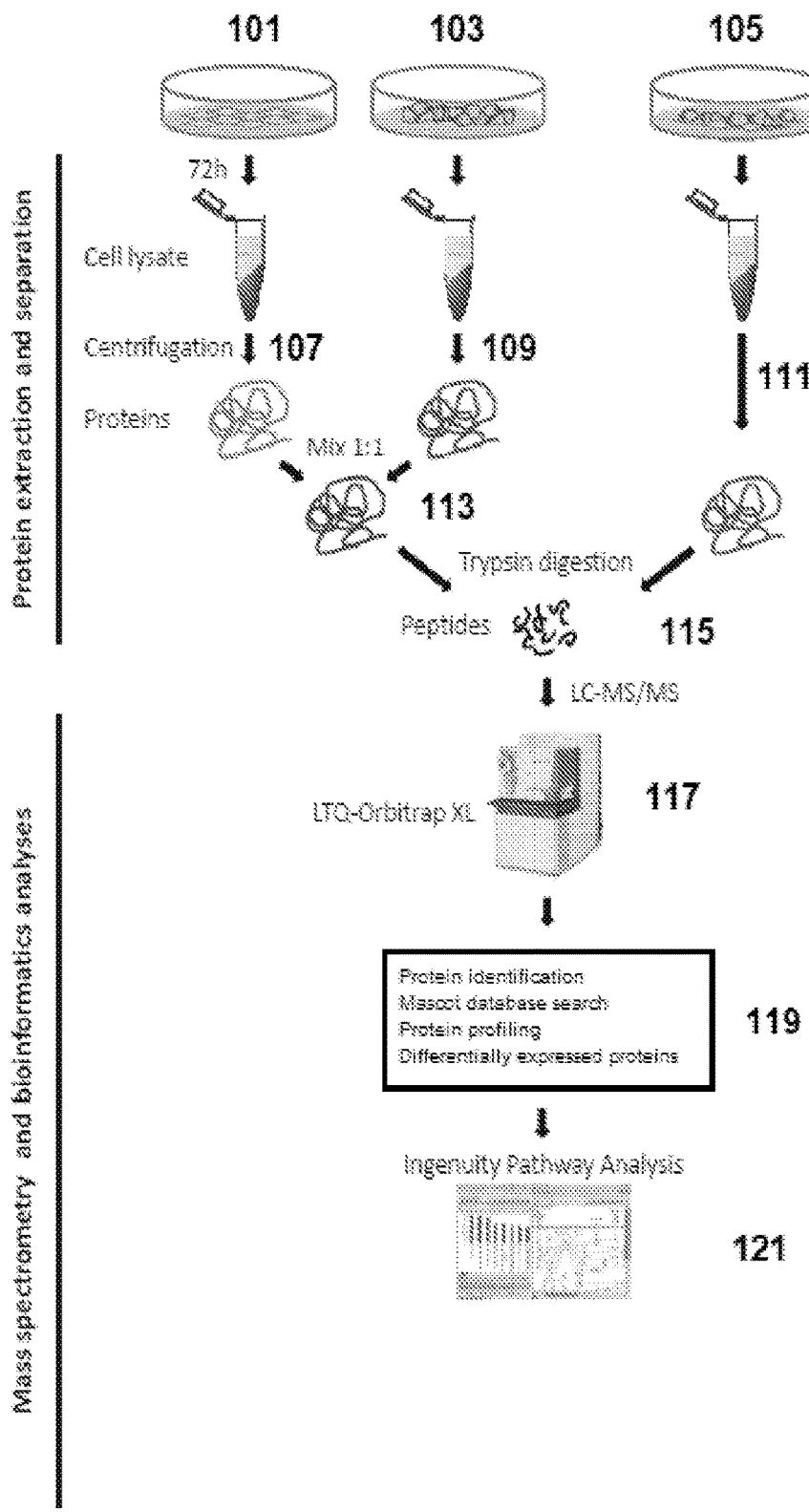
FIG. 1 shows a work-flow schematic of an embodiment of the present approach.

The following description illustrates embodiments of the present approach in sufficient detail to enable practice of the present approach. Although the present approach is described with reference to these specific embodiments, it should be appreciated that the present approach can be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

In the embodiments disclosed herein, MCF7-fibroblast co-cultures were used as a model system to dissect the molecular basis of Tamoxifen-resistance. MCF7-fibroblasts co-cultures are protected against apoptosis induced by hormonal therapies, such as Tamoxifen and Fulvestrant. This resistance can be reversed by using Metformin, a known mitochondrial inhibitor. Metformin acts as an OXPHOS inhibitor and activates AMP-kinase, by functionally inactivating mitochondrial Complex I activity. However, the molecular targets that confer resistance to hormonal therapy in this epithelial-stromal model have remained elusive, although it was noted that mitochondrial mass was increased in MCF7 cells, as seen by vital staining with the probe MitoTracker.

As described herein, the MCF7-fibroblast co-culture system was subjected to unbiased label-free proteomics analysis to identify potential new therapeutic targets. The induction of both "mito-stemness" and "ribo-stemness" features—associated with CSCs—were seen in the co-cultures, consistent with the induction of a more stem-like phenotype. In further support of this notion, the epithelial CSC marker KRT19 was induced nearly 6-fold. KRT19 is currently used clinically to identify metastatic breast cancer cells in sentinel lymph-node biopsies.

The specific candidate targets identified by proteomics analysis were then intersected with a wealth of publically-available clinical data, first to validate their expression in human breast cancer cells in vivo. These clinical samples were first subjected to laser-capture micro-dissection to separate human breast cancer cells, from adjacent tumor stroma, before they were subjected to mRNA-based transcriptional profiling.

The targets identified by proteomics were then used to construct a mitochondrial gene signature, to assess whether the candidate biomarkers could be used as companion diagnostics for Tamoxifen-resistance. Using publically-available clinical outcome data, the prognostic value of the resulting 3-gene Mito-Signature was stringently evaluated. As shown herein, this Mito-Signature effectively predicted tumor recurrence and distant metastasis in breast cancer patients that were treated with Tamoxifen or hormonal therapy. The development of recurrence or metastasis during Tamoxifen treatment is a clear sign of treatment failure and is an accepted clinical hallmark of Tamoxifen-resistance.

Also described herein are treatment strategies to selectively sensitize MCF7 cells in co-culture, based on their apparent increase in mitochondrial biogenesis. For this purpose, a co-culture system employing fluorescently-labeled MCF7 cells and fibroblasts was used. In this system, MCF7 cells expressing GFP were co-cultured with hTERT-BJ1 fibroblasts expressing RFP, so that these two cellular components were easily distinguishable.

Certain FDA-approved antibiotics that target host protein synthesis and mitochondrial protein translation as off-target side effects demonstrated an ability to sensitize MCF7 cells, under co-culture conditions. The results indicate that MCF7 cells in co-culture were ~5-fold more sensitive to the effects of Doxycycline and ~8-fold more sensitive to the effects of Azithromycin. Additionally, conjugating these drugs with a targeting signal increases this effect. Consequently, the targeting of mitochondrial protein translation via drug repurposing is an effective anti-cancer strategy, especially under these more physiologically-relevant culture conditions, which includes a stromal tumor-microenvironment.

Other recent studies using mono-cultures of MCF7 cells have also suggested a role for increased mitochondrial OXPHOS, in conferring Tamoxifen-resistance. For example, Tamoxifen-resistant MCF7 cells, derived from long-term cell culture with increasing concentrations of Tamoxifen, showed an increase in mitochondrial mass and mitochondrial-dependent ATP production. Similarly, over-expression of a somatic mutation of the estrogen receptor (ESR1-Y537S) normally associated with the clinical development of Tamoxifen-resistance in patients, also increased mitochondrial mass and mitochondrial-dependent ATP production. Therefore, three independent models of Tamoxifen-resistance mechanistically appear to show the same or a very similar mitochondrial phenotype. As such, this highly-suggestive data implies that mitochondrial inhibitors, including those described herein, should be tested clinically as a possible therapeutic option for the prevention and/or treatment of Tamoxifen-resistance or perhaps other forms of hormonal therapy resistance.

In this context, it is interesting to note that one of the recognized off-target side effects of Tamoxifen is that it behaves as a bonafide inhibitor of mitochondrial complex III and complex IV, while simultaneously inducing oxidative stress. Therefore, Tamoxifen treatment itself may lead to drug resistance, simply by stimulating mitochondrial biogenesis in response to its own intrinsic anti-mitochondrial activity, rather than via its direct or targeted effects on ER-alpha signaling.

This description uses various terms that should be understood by those of an ordinary level of skill in the art. The following clarifications are made for the avoidance of doubt. The terms "treat," "treated," "treating," and "treatment" include the diminishment or alleviation of at least one symptom associated or caused by the state, disorder or disease being treated, in particular, cancer. In certain embodiments, the treatment comprises diminishing and/or alleviating at least one symptom associated with or caused by the cancer being treated, by the compound of the invention. In some embodiments, the treatment comprises causing the death of a category of cells, such as CSCs, of a particular cancer in a host, and may be accomplished through preventing cancer cells from further propagation, and/or inhibiting CSC function through, for example, depriving such cells of mechanisms for generating energy. For example, treatment can be diminishment of one or several symptoms of a cancer, or complete eradication of a cancer.

The terms "cancer stem cell" and "CSC" refer to the subpopulation of cancer cells within tumors that have capabilities of self-renewal, differentiation, and tumorigenicity when transplanted into an animal host. Compared to "bulk" cancer cells, CSCs have increased mitochondrial mass, enhanced mitochondrial biogenesis, and higher activation of mitochondrial protein translation. As used herein, a "circulating tumor cell" is a cancer cell that has shed into the vasculature or lymphatics from a primary tumor and is carried around the body in the blood circulation. The CellSearch Circulating Tumor Cell Test may be used to detect circulating tumor cells.

The phrase "pharmaceutically effective amount," as used herein, indicates an amount necessary to administer to a host, or to a cell, tissue, or organ of a host, to achieve a therapeutic result, such as regulating, modulating, or inhibiting protein kinase activity, e.g., inhibition of the activity of a protein kinase, or treatment of cancer. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

As used herein, the phrase "active compound" refers to the therapeutic compound used in connection with a treatment described herein, which may include a pharmaceutically acceptable salt or isotopic analog thereof. It should be appreciated that the active compound(s) may be administered to the subject through any suitable approach, as would be known to those having an ordinary level of skill in the art. It should also be appreciated that the amount of active compound and the timing of its administration may be dependent on the individual subject being treated (e.g., the age and body mass, among other factors), on the manner of administration, on the pharmacokinetic properties of the particular active compound(s), and on the judgment of the prescribing physician. Thus, because of subject to subject variability, any dosages described herein are intended to be initial guidelines, and the physician can titrate doses of the compound to achieve the treatment that the physician considers appropriate for the subject. In considering the degree of treatment desired, the physician can balance a variety of factors such as age and weight of the subject, presence of preexisting disease, as well as presence of other diseases. Pharmaceutical formulations can be prepared for any desired route of administration including, but not limited to, oral, intravenous, or aerosol administration, as discussed in greater detail below.

The following paragraphs describe the use proteomics to identify proteins up-regulated in MCF7-fibroblast co-cultures. Cancer cells, grown in close proximity to fibroblasts, metabolically reprogram these fibroblasts towards a more catabolic state, via the induction of autophagy, mitophagy, and glycolysis, as well as senescence. Conversely, through this interaction, cancer cells undergo reciprocal metabolic reprogramming towards a more anabolic state, with the induction of mitochondrial biogenesis and oxidative metabolism. This metabolic co-operation primarily benefits the cancer cells by providing nutrients to generate new biomass. Unfortunately, most of the metabolic targets in this symbiotic process remain completely unknown.

Described herein is an approach to identify such therapeutic targets, via unbiased proteomics analysis. For this purpose, MCF7 cells, an ER(+) human breast cancer cell line, may be used as a model system. With respect to the results discussed herein, MCF7 cells were co-cultured with hTERT-BJ1 fibroblasts, in a cellular ratio of 1:1, for a short 3-day period. These MCF7-fibroblast co-cultures were then directly compared to a 1:1 protein mixture of MCF7 cells and hTERT-fibroblasts that had not been co-cultured together but grown instead as homotypic mono-cultures.

FIG. 1 shows a diagram summarizing the work-flow for MCF7-fibroblast co-culture studies and bioinformatics validation as used in the present approach. Samples of hTERT-BJ1 fibroblasts 101, MCF7 breast cancer cells 103, and co-cultured hTERT-BJ1/MCF7 105, were prepared. hTERT-BJ1 fibroblasts after 72 h co-culture with MCF7 breast cancer cells. Protein lysates 111 were obtained from the co-culture sample, and protein lysates 107 and 109 were obtained from hTERT-BJ1 fibroblasts 101 and MCF7 cells 103 cultured separately as monolayers and then mixed 113. Peptides 115 were obtained after trypsin digestion, and then analyzed LC-MS/MS on an LTQ-Orbitrap XL mass spectrometer 117. Label-free quantitative proteomics 119 was used to detect changes in protein abundances across co-cultures and mixed cell population extracts. The proteomics data sets were further analyzed using Ingenuity Pathway Analysis 121. This co-culture approach better simulates the fibroblast-rich local tumor micro-environment in vivo, compared to the mixed population extracts.

To a first approximation, using proteomics, this approach allows for an identification of the proteins that are increased during the co-culture process, relative to mono-cultures. Then, these protein candidates may be compared with human breast cancer samples that had undergone laser-capture micro-dissection, to validate their relevant expression in human breast cancer cells in vivo. For the results discussed herein, publically-available transcriptional-profiling data (from N=28 breast cancer patients; See Materials and Methods) were used.

Figure 2:
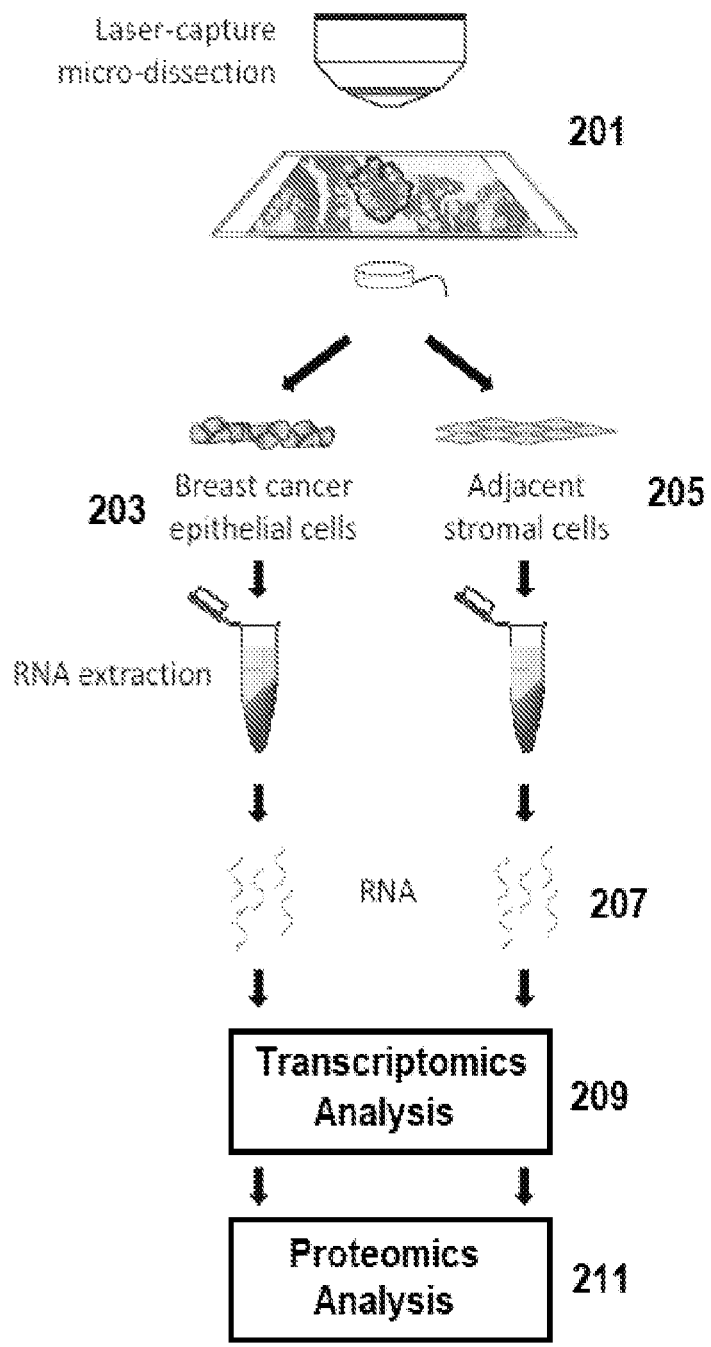
FIG. 2 is a work-flow schematic for validation through transcriptional profiling.

FIG. 2 illustrates the work-flow for validation studies. Patient-derived breast primary tumor samples 201 were acquired through laser-capture micro-dissection. Data from N=28 patient-derived breast primary tumor samples. From these samples, target cell populations were collected, including breast cancer epithelial cells 203 and adjacent stromal cells 205. RNA 207 were extracted from these cells and subjected to transcriptomics analysis 209 and proteomics analysis 211.

Mitochondrial biogenesis is induced in MCF7 cells when they are co-cultured with fibroblasts. Previously, it was unknown exactly which mitochondrial proteins are induced during co-culture. Therefore, the analysis first focused on which mitochondrial proteins were increased during co-culture, based on this proteomics approach.

Table 1 illustrates the 45 mitochondrial-related proteins that were found to be significantly up-regulated during the MCF7-fibroblast co-culture process. This list includes proteins that are involved in mitochondrial biogenesis and/or are part of the mitochondrial complexes I to V, as well as mitochondrial chaperones, such as DNAJA3, HSPD1 and HSPA9, among others. Interestingly, NDUFAF2, a MYC-induced component of complex I, was infinitely up-regulated during co-culture. The co-culture of MCF7 cells with fibroblasts confers a Tamoxifen-resistance that is reversible by treatment with Metformin, a complex I inhibitor. Therefore, NDUFAF2 (a.k.a, Mimitin) may be functionally conferring Tamoxifen-resistance during co-culture.

TABLE 1

Proteomics Analysis: Mitochondrial-Related Proteins Up-regulated in MCF7-Fibroblast Co-Cultures.

| Gene Symbol | Description | Fold-Increase | Mito-Complex | MRP/Chaperone |
|---|---|---|---|---|
| NDUFAF2 | Mimitin, c-Myc-induced mitochondrial protein; B17.2L (related to NDUFAF4/HRPAP20) | Infinity | I | Chaperone |
| GPD2 | Glycerol-3-phosphate dehydrogenase, mitochondrial (ROS/H2O2 Production) | 238.91 | | |
| AIFM1 | Apoptosis-inducing factor 1, mitochondrial (NADH oxidase activity) | 237.74 | I, III, IV | Chaperone |
| PRKDC | DNA-dependent protein kinase catalytic subunit (mitochondrial genome maintenance) | 102.78 | | |
| DNAJA3 | HSP40, DnaJ homolog, subfamily A, member 3, mitochondrial | 76.43 | | Chaperone |
| MRPL43 | Mitochondrial ribosomal protein L43 | 66.38 | | MRP |
| COX4I1 | Cytochrome c oxidase subunit 4 isoform 1 | 56.68 | IV | |

TABLE 1-continued

Proteomics Analysis: Mitochondrial-Related Proteins Up-regulated in MCF7-Fibroblast Co-Cultures.

| Gene Symbol | Description | Fold-Increase | Mito-Complex | MRP/Chaperone |
|---|---|---|---|---|
| HSPD1 | HSP60, 60 kDa heat shock protein, mitochondrial | 29.29 | | Chaperone |
| MRRF | Ribosome-recycling factor, mitochondrial | 23.53 | | MRP |
| SLC25A5 | Solute Carrier Family 25 (Mitochondrial Carrier; ADP/ATP Translocator), Member 5 | 14.49 | | |
| VDAC2 | Voltage-dependent anion-selective channel protein 2 | 13.6 | | |
| UQCRFS1 | RISP, Ubiquinol-cytochrome C reductase iron-sulfur subunit, (Rieske iron-sulfur protein) | 13.07 | III | |
| VDAC1 | Voltage-dependent anion-selective channel protein 1 | 10.05 | | |
| ECH1 | Delta(3,5)-Delta(2,4)-dienoyl-CoA isomerase, mitochondrial | 8.51 | | |
| MCCC2 | Methylcrotonoyl-CoA carboxylase beta chain, mitochondrial | 4.52 | | |
| MRPS28 | MRPS28 protein | 3.86 | | MRP |
| ATP5A1 | ATP synthase subunit alpha, (EC 3.6.3.14) | 3.83 | V | |
| SUCLG2 | Succinyl-CoA ligase [GDP-forming] subunit beta, mitochondrial | 3.58 | | |
| ABAT | 4-aminobutyrate aminotransferase, mitochondrial | 3.44 | | |
| IMMT | Mitochondrial inner membrane protein | 3.27 | | |
| AK4 | Adenylate kinase isoenzyme 4, mitochondrial | 3.02 | | |
| GOT2 | Aspartate aminotransferase, mitochondrial | 2.87 | | |
| HSPA9 | heat shock 70 kDa protein 9 (mortalin), mitochondrial | 2.47 | | Chaperone |
| TUFM | Elongation factor Tu, mitochondrial | 2.37 | | |
| CLUH | Clustered mitochondria protein homolog | 2.15 | | |
| OAT | Ornithine aminotransferase, mitochondrial | 2.14 | | |
| IDH1 | Isocitrate dehydrogenase [NADP], cytoplasmic | 2.1 | | |
| SLC25A3 | Solute carrier family 25 (mitochondrial carrier; phosphate carrier), member 3 | 2.09 | | |
| NDUFA5 | NADH dehydrogenase [ubiquinone] 1 alpha subcomplex subunit 5 | 2.08 | I | |
| UQCRC2 | Cytochrome b-c1 complex subunit 2, mitochondrial | 2.07 | III | |
| ETFA | Electron transfer flavoprotein subunit alpha, mitochondrial | 2.05 | | |
| PPA2 | Inorganic pyrophosphatase 2, mitochondrial | 2.03 | | |
| ECHS1 | Enoyl-CoA hydratase, mitochondrial | 2.02 | | |
| PPT1 | Palmitoyl-protein thioesterase 1 | 1.91 | | |
| DLD | Dihydrolipoyl dehydrogenase, mitochondrial | 1.89 | | |
| CHCHD3 | Coiled-coil-helix-coiled-coil-helix domain-containing protein 3, mitochondrial | 1.89 | | |
| ATP5H | ATP synthase subunit d, mitochondrial | 1.88 | V | |
| IARS2 | Isoleucine--tRNA ligase, mitochondrial | 1.86 | | |
| LRPPRC | Leucine-rich PPR-motif containing, mitochondrial | 1.85 | | |
| PC | Pyruvate carboxylase, mitochondrial | 1.79 | | |
| HADHA | Trifunctional enzyme subunit alpha, mitochondrial | 1.74 | | |
| SLC25A13 | Calcium-binding mitochondrial carrier protein Aralar2 | 1.74 | | |
| TRAP1 | Heat shock protein 75 kDa, mitochondrial | 1.72 | | Chaperone |
| ACADSB | Short/branched chain specific acyl-CoA dehydrogenase, mitochondrial | 1.72 | | |
| CPT1A | Carnitine palmitoyltransferase 1A, mitochondrial | 1.65 | | |

The Proteins listed above in Table 1 (45 in total) were all upregulated in MCF7-Fibroblast Co-cultures (p<0.05). The acronym "MRP" identifies mitochondrial ribosomal proteins. Increased mitochondrial biogenesis is a hallmark of CSCs, known as "mito-stemness," and as a result, the next focus was identifying markers of protein synthesis. Protein synthesis is another hallmark of CSCs, referred to herein as "ribo-stemness."

Table 2 shows that 28 components of the large and small cellular ribosomal subunits were up-regulated during co-culture. More specifically, 18 components of the large 60S ribosome and 10 components of the small 40S ribosome were increased. As can be seen, RPL4 and RPS29 were infinitely increased during co-culture.

TABLE 2

Proteomics Analysis: Ribosomal Proteins Up-regulated in MCF7-Fibroblast Co-Cultures.

| Gene Symbol | Description | Fold-Increase |
|---|---|---|
| RPL4 | 60S ribosomal protein L4 | Infinity |
| RPL15 | 60S ribosomal protein L15 | 2,238.12 |
| RPL19 | 60S ribosomal protein L19 | 168.84 |
| RPL36AL | 60S ribosomal protein L36a-like | 54.47 |
| RPL24 | 60S ribosomal protein L24 | 43.56 |
| RPL10 | 60S ribosomal protein L10 | 42.78 |
| RPL29 | 60S ribosomal protein L29 | 20.53 |
| RPL18A | 60S ribosomal protein L18a | 17.08 |
| RPL8 | 60S ribosomal protein L8 | 5.74 |
| RPL34 | 60S ribosomal protein L34 | 5.36 |
| RPL13 | 60S ribosomal protein L13 | 5.31 |
| RPL14 | 60S ribosomal protein L14 | 3.09 |
| RPL3 | 60S ribosomal protein L3 | 3.04 |
| RPL27a | 60S ribosomal protein L27a | 2.99 |
| RPLP2 | 60S acidic ribosomal protein P2 | 2.9 |
| RPL6 | 60S ribosomal protein L6 | 2.05 |
| RPL5 | 60S ribosomal protein L5 | 2.04 |
| RPL28 | 60S ribosomal protein L28 | 2 |
| RPS29 | 40S ribosomal protein S29 | Infinity |
| RPS10 | 40S ribosomal protein S10 | 74.47 |
| RPS6 | 40S ribosomal protein S6 | 23.37 |
| RPS18 | 40S ribosomal protein S18 | 9.2 |
| RPS27A | 40S ribosomal protein S27a | 5.19 |
| RPS2 | 40S ribosomal protein S2 | 2.98 |
| RPS27A | 40S ribosomal protein S27a | 2.96 |
| RPS3A | 40S ribosomal protein S3A | 2.39 |
| RPS19 | 40S ribosomal protein S19 | 2.05 |
| RPS11 | 40S ribosomal protein S11 | 2 |

The proteins listed above in Table 2 (28 in total) were all upregulated in MCF7-Fibroblast Co-cultures (p<0.05). Consistent with the findings shown in Tables 1 and 2, protein-folding chaperones were also induced. Table 3 lists 10 chaperones that were significantly increased during co-culture. These include members of the HSP90 and HSP70 families of chaperones, as well as others. Remarkably, HSP90AB1 was infinitely up-regulated. The 10 proteins listed in Table 3 below were all upregulated in MCF7-Fibroblast Co-cultures (p<0.05).

TABLE 3

Proteomics Analysis: Other Chaperones Up-regulated in MCF7-Fibroblast Co-Cultures.

| Gene Symbol | Description | Fold-Increase |
|---|---|---|
| HSP90AB1 | Heat Shock Protein 90 kDa Alpha (Cytosolic), Class B Member 1 | Infinity |
| HSPA5 | 78 kDa glucose-regulated protein | 82.18 |
| HSP90AA1 | Heat Shock Protein 90 kDa Alpha (Cytosolic), Class A Member 1 | 79.52 |
| HSPB1 | Heat Shock 27 kDa Protein 1 | 35.73 |
| HSPA8 | Heat shock cognate 71 kDa protein | 8.42 |
| HSPA4 | Heat shock 70 kDa protein | 5.38 |
| STIP1 | Stress-induced-phosphoprotein 1 (HS P70/HS P90-org anizing protein) | 2.99 |
| CDC37 | HSP90 co-chaperone Cdc37 | 2.83 |
| HSPA2 | Heat shock-related 70 kDa protein 2 | 2.59 |
| HSPH1 | Heat shock protein 105 kDa | 2.53 |

Similarly, Table 4 shows that proteins involved in mRNA translation initiation, polypeptide elongation, tRNA synthesis and amino acid uptake were all significantly up-regulated during co-culture. Overall, this includes 30 proteins in total. For example, EIF2S1, a translation initiation factor required for mRNA binding to ribosomes, was increased by nearly 300-fold.

TABLE 4

Proteomics Analysis: Proteins Involved in mRNA Translation Initiation, Polypeptide Elongation, tRNA Synthesis and Amino Acid Uptake are All Up-regulated in MCF7-Fibroblast Co-Cultures.

| Gene Symbol | Description | Fold-Increase |
|---|---|---|
| *Translation initiation factors (required for mRNA binding to ribosomes)* | | |
| EIF2S1 | Eukaryotic translation initiation factor 2 subunit 1 | 291.47 |
| EIF3H | Eukaryotic translation initiation factor 3 subunit H | 81.05 |
| EIF4H | Eukaryotic translation initiation factor 4H | 31.21 |
| EIF4A1 | Eukaryotic translation initiation factor 4A-I | 18.85 |
| EIF5 | Eukaryotic translation initiation factor 5 | 8.72 |
| EIF3A | Eukaryotic translation initiation factor 3 subunit A | 2.94 |
| EIF2S3L | Putative eukaryotic translation initiation factor 2 subunit 3-like protein | 2.86 |
| EIF3E | Eukaryotic translation initiation factor 3 subunit E | 2.3 |
| EIF3B | Eukaryotic translation initiation factor 3 subunit B | 1.85 |
| *Elongation factors (promote delivery of aminoacyl tRNAs to the ribosome)* | | |
| EEF2 | Elongation factor 2 | 18.96 |
| EEF1G | Elongation factor 1-gamma | 2.45 |
| TUFM | Elongation factor Tu, mitochondrial | 2.37 |
| EEF1A2 | Elongation factor 1-alpha 2 | 2.36 |
| EEF1A1 | Elongation factor 1-alpha | 2.03 |
| EEF1D | Elongation factor 1-delta | 1.86 |
| *Enzymes for tRNA Synthesis* | | |
| QARS | Glutamine--tRNA ligase, cytoplasmic | 31.9 |
| DARS | Aspartate--tRNA ligase, cytoplasmic | 9.69 |
| MARS | Methionine-tRNA synthetase, cytoplasmic | 3.44 |
| RTCB | tRNA-splicing ligase RtcB homolog (C22orf28) | 3.25 |
| DTD1 | D-tyrosyl-tRNA(Tyr) deacylase 1 | 3.1 |
| YARS | Tyrosine--tRNA ligase, cytoplasmic | 2.38 |
| RARS | Arginine--tRNA ligase, cytoplasmic | 2.23 |
| AARS | Alanyl-tRNA synthetase, cytoplasmic | 2.23 |
| IARS2 | Isoleucine--tRNA ligase, mitochondrial | 1.86 |
| AIMP2 | Aminoacyl tRNA synthase complex-interacting multifunctional protein 2 | 1.7 |
| GARS | Glycine--tRNA ligase, cytoplasmic | 1.7 |
| EPRS | Bifunctional glutamate/proline--tRNA ligase | 1.67 |
| TRMT112 | tRNA methyltransferase 112 homolog | 1.66 |
| *Amino Acid Transporters* | | |
| SLC6A19 | Neutral amino acid transporter B(0) | 4.18 |
| SLC7A5 | Solute carrier family 7 (Cationic AA transporter, y+ system), member 5 | 3.05 |

The 30 proteins listed in Table 4 were all upregulated in MCF7-Fibroblast Co-cultures (p<0.05). Furthermore, other well-known markers of "stemness" and proliferation were increased, as shown in Table 5, below. More specifically, MKI67 was increased by >4,000-fold, while KRT19 and PCNA were increased by nearly 6-fold and 4-fold, respectively. The profound increase in MKI67 is more consistent with increased protein synthesis, rather than increased proliferation. MKI67 is expressed in all cycling cells, except for resting cells in the G0-phase and is specifically associated with ribosomal RNA (rRNA) synthesis and, thus, protein synthesis. This is consistent with the results presented in Tables 2-4. In this context, KRT19 is a well-established epithelial CSC marker that is used clinically to identify metastatic breast cancer cells in sentinel lymph node biopsies. These data and observations are consistent with the idea that MCF7-fibroblast co-cultures increase their biosynthetic cellular machinery (i.e., mitochondria and ribosomes), to expand their anabolic capacity to increase their biomass.

TABLE 5

Proteomics Analysis: Markers of Cell Proliferation and Stemness are Up-regulated in MCF7-Fibroblast Co-Cultures.

| Gene Symbol | Description | Fold-Increase | Specificity |
|---|---|---|---|
| MKI67 | Antigen KI-67 | 4,531.38 | Expressed in all cycling cells, except for resting cells in the G0-phase; Associated also with ribosomal RNA (rRNA) synthesis and, thus, protein synthesis |
| KRT19 | Keratin, type I cytoskeletal 19 | 5.94 | Marker of CSCs and breast cancer metastasis (sentinel lymph node) |
| PCNA | Proliferating cell nuclear antigen | 3.87 | Marker for the G1/S phase of the cell cycle |

Figure 3A:
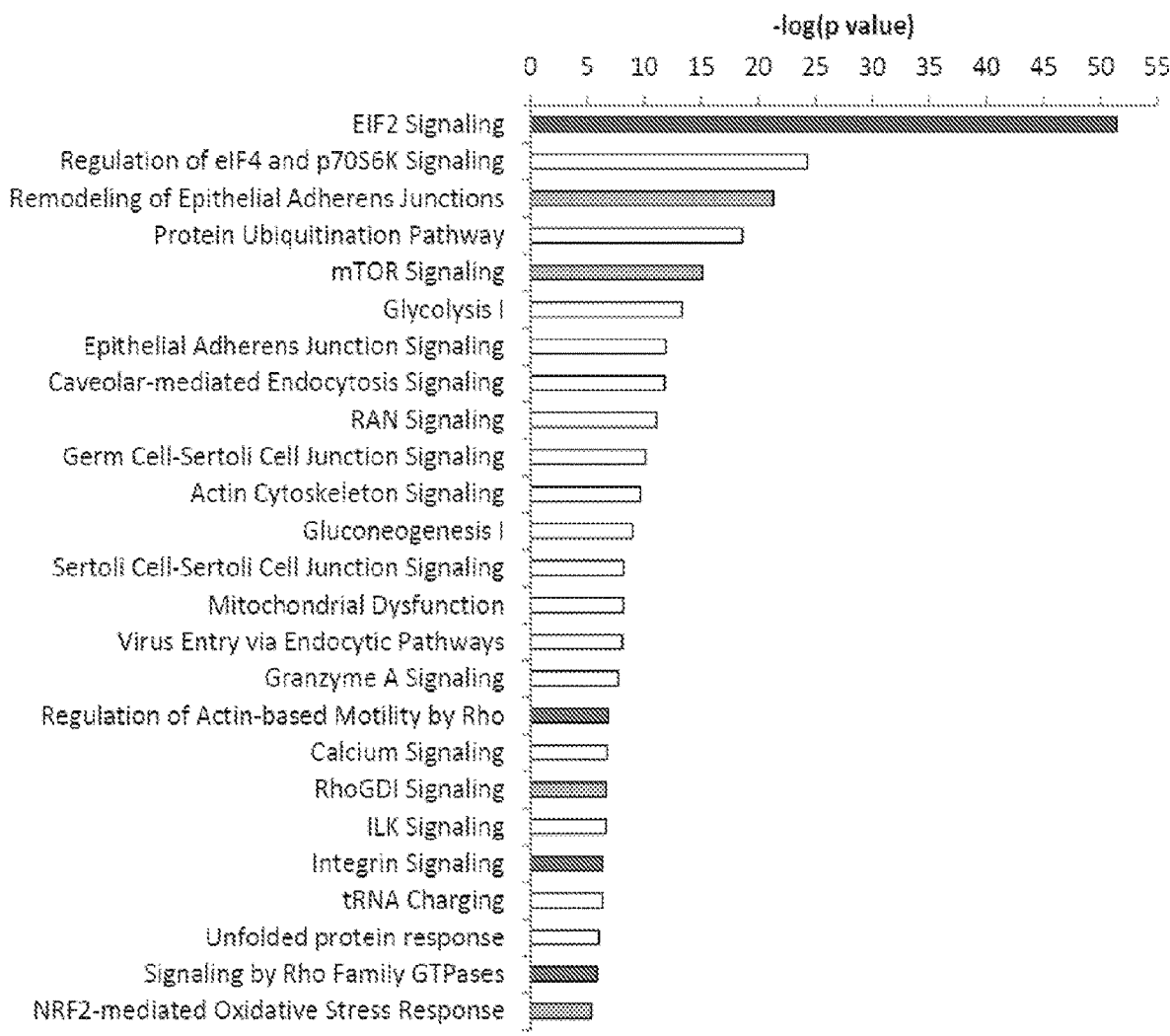
FIGS. 3A and 3B summarize Ingenuity Pathway Analysis (IPA) of differentially expressed proteins in co-cultures compared to mixed cell populations.
Figure 3B:
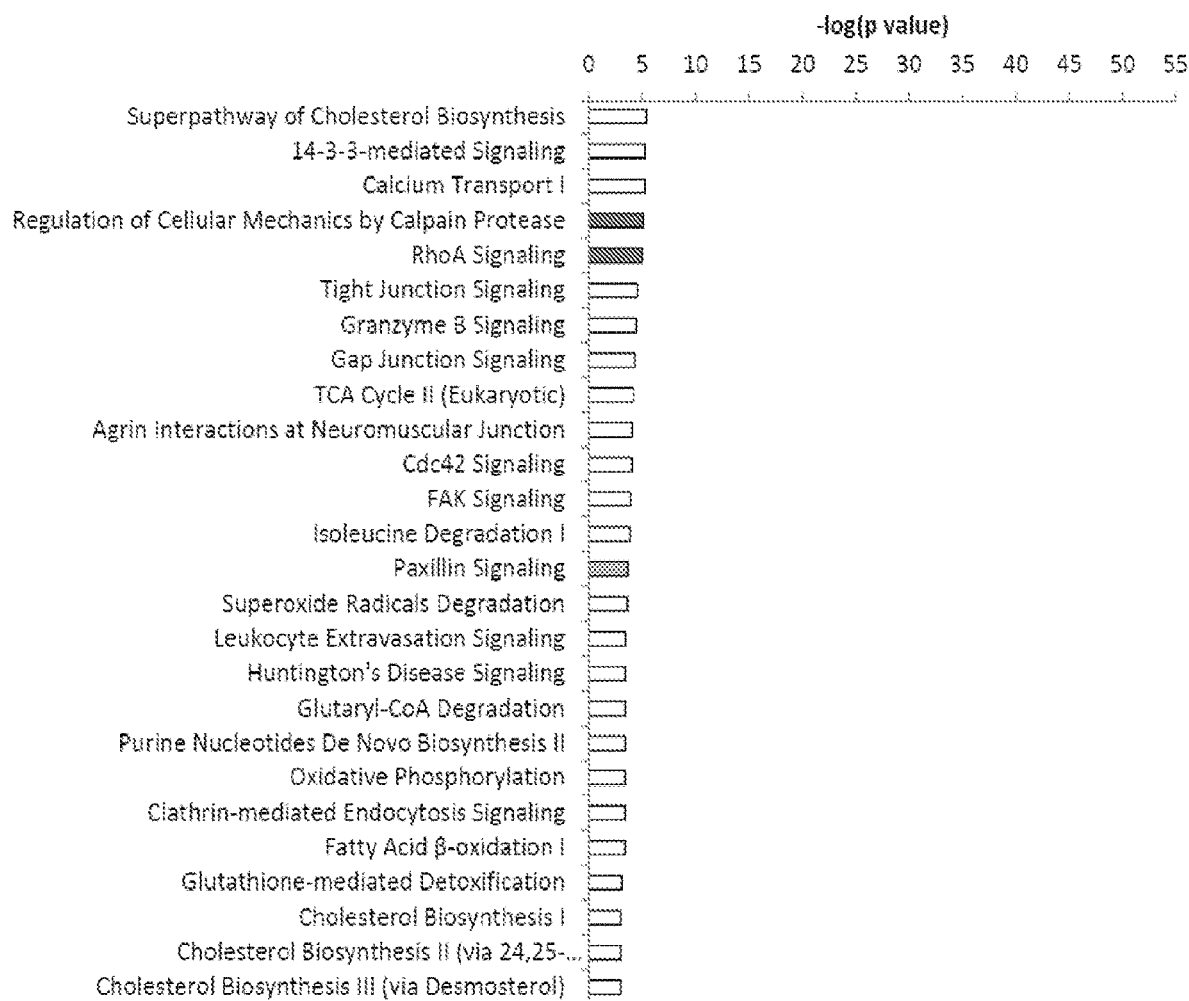

Differentially expressed proteins were independently analyzed using Ingenuity Pathway Analysis (IPA), to identify altered canonical pathways and toxicity functions. This analysis revealed that EIF2 signaling, which is crucial for protein synthesis, is a significantly activated canonical pathway in co-cultures, as compared to mono-cultures, as measured by a z-score>2 and shown in FIGS. 3A and 3B. These figures summarize Ingenuity Pathway Analysis (IPA) of differentially expressed proteins in co-cultures compared to mixed cell populations, and show canonical pathways significantly altered (p<0.001). The p value for each pathway is indicated by the bar and is expressed as −1 times the log of the p value. The bar for EIF2 Signaling indicates a predicted significant activation of the pathway (z-score>2), whereas the shaded bars for Remodeling of Epithelial Adherens Junctions, mTOR Signaling, RhoGDI Signaling, NRF2-mediated Oxidative Stress Response, and Paxilin Signaling, indicate a not significant activation (z-score between 0 and 2). The shaded bars for Regulation of Actin-based Motility by Rho, Integrin Signaling, Signaling by Rho Family GTPases, Regulation of Cellular Mechanics by Calpain Release, and RhoA Signaling, indicate a not significant inhibition of the pathway (z-score between 0 and −2). White bars indicate that the pathway is altered, but it was not possible to predict whether it is activated nor inhibited.

Figure 4:
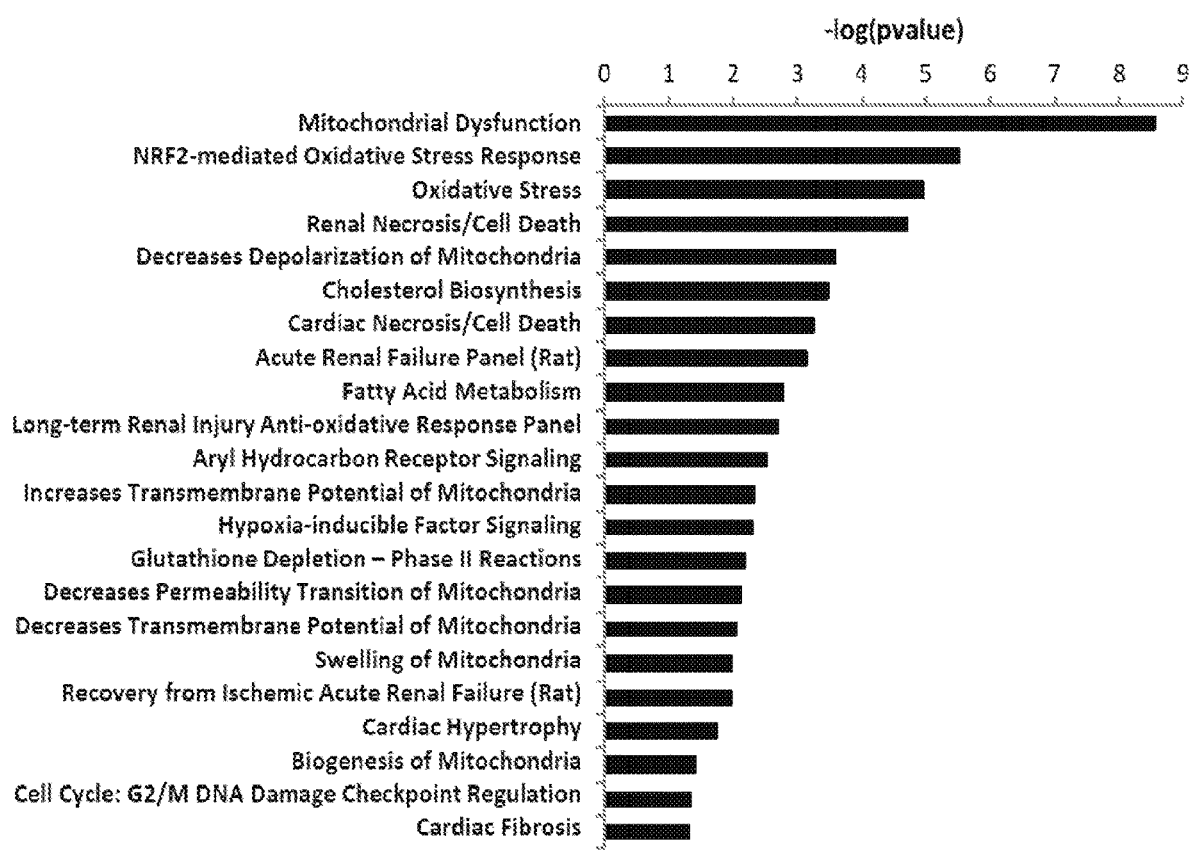
FIG. 4 shows the "toxicity" effects of differentially expressed proteins in co-cultures versus monocultures.

Other altered pathways and toxicity functions identified by IPA included mitochondrial dysfunction, NRF2-mediated oxidative stress, fatty acid metabolism, changes in mitochondrial membrane potential, HIF signaling, glutathione depletion, mitochondrial biogenesis, DNA-damage and fibrosis, among others. FIG. 4 shows "toxicity" effects of differentially expressed proteins in co-cultures versus mono-cultures. The IPA showed toxicity functions significantly enriched by the proteins differentially expressed in co-cultures ($P<0.05$). The p value for each pathway is indicated by the bar and is expressed as −1 times the log of the p value. These results are consistent with the induction of "mito-stemness" and "ribo-stemness" features during the co-culture process.

The next paragraphs describe validating the clinical relevance of co-culture proteomics data, using patient-derived breast tumor samples. Transcriptional profiling data were used to directly validate the potential clinical relevance of these findings. The data were derived from the analysis of N=28 breast cancer patients, which were previously subjected to laser-capture micro-dissection, to physically separate breast cancer cells from adjacent stromal cells. The proteomics data was intersected with this clinical data set. Tables 6-9 below show the levels of fold-upregulation observed in the epithelial cancer cell compartment (relative to the tumor stroma), and corresponding p-values derived from these clinical samples.

Table 6 shows that of the 45 mitochondrial proteins that were up-regulated during co-culture, 34 were also significantly increased by >1.75-fold in human breast cancer cells in vivo. Therefore, >75% of the mitochondrial proteins elevated during co-culture were transcriptionally increased in patient-derived breast cancer cells in vivo.

TABLE 6

Supplemental TABLE 6. Nuclear Mitochondrial Gene Transcripts Up-regulated in Human Breast Cancers (Cancer Epithelia vs. Tumor Stroma).

| Gene Symbol | Fold-Increase | P-Value |
|---|---|---|
| UQCRFS1 | 5.71 | 2.45E−07 |
| MCCC2 | 5.48 | 5.78E−07 |
| ATP5A1 | 5.01 | 3.09E−06 |
| UQCRC2 | 4.84 | 5.73E−06 |
| IMMT | 4.71 | 8.89E−06 |
| IARS2 | 4.70 | 9.15E−06 |
| GOT2 | 4.58 | 1.40E−05 |
| LRPPRC | 4.34 | 3.15E−05 |
| ECHS1 | 4.05 | 8.22E−05 |
| ATP5H | 4.01 | 9.48E−05 |
| VDAC2 | 3.99 | 0.0001 |
| DLD | 3.78 | 0.0002 |
| PPT1 | 3.76 | 0.0002 |
| SLC25A3 | 3.76 | 0.0002 |
| HSPA9 | 3.69 | 0.0002 |
| SLC25A5 | 3.49 | 0.0005 |
| HSPD1 | 3.42 | 0.0006 |
| COX4I1 | 3.39 | 0.0007 |
| TUFM | 3.38 | 0.0007 |
| HADHA | 3.27 | 0.0009 |
| PPA2 | 3.19 | 0.001 |
| IDH1 | 3.18 | 0.001 |
| OAT | 3.17 | 0.001 |
| SUCLG2 | 3.03 | 0.002 |
| DNAJA3 | 2.92 | 0.003 |
| NDUFA5 | 2.75 | 0.004 |
| CHCHD3 | 2.74 | 0.004 |
| SLC25A13 | 2.69 | 0.005 |
| VDAC1 | 2.64 | 0.005 |
| MRPS28 | 2.25 | 0.01 |
| PRKDC | 2.14 | 0.02 |
| ABAT | 2.08 | 0.02 |
| ECH1 | 1.97 | 0.03 |
| ETFA | 1.75 | 0.04 |

In Table 6, the transcriptional profiling data derived from the analysis of N=28 breast cancer patients are shown, highlighting the levels of fold-upregulation observed in the epithelial cancer cell compartment (relative to the tumor stroma), and corresponding p-values derived from the analysis of these clinical samples. The Proteins listed in Table 6 (34 in total) were all upregulated in MCF7-Fibroblast Co-cultures (Compare with Supplemental Table 1) ($p<0.05$).

Table 7 highlights that of the 28 ribosomal proteins that were up-regulated during co-culture, 27 were significantly increased by >1.7-fold in human breast cancer cells in vivo. Thus, >96% of the ribosomal proteins elevated during co-culture were transcriptionally increased in human breast cancer cells in vivo. Transcriptional profiling data derived from the analysis of N=28 breast cancer patients are shown, high-lighting the levels of fold-upregulation observed in the epithelial cancer cell compartment (relative to the tumor stroma), and corresponding p-values derived from the analysis of these clinical samples. The 27 proteins listed in Table 7 were all upregulated in MCF7-Fibroblast Co-cultures ($p<0.05$).

TABLE 7

Ribosomal Protein Gene Transcripts Up-regulated in Human Breast Cancers (Cancer Epithelia vs. Tumor Stroma).

| Gene Symbol | Fold-Increase | P-Value |
|---|---|---|
| RPL24 | 5.38 | 8.11E−07 |
| RPL3 | 5.01 | 3.14E−06 |
| RPL10 | 4.91 | 4.48E−06 |
| RPL15 | 4.60 | 1.28E−05 |
| RPL13 | 4.48 | 1.98E−05 |
| RPL14 | 4.45 | 2.15E−05 |
| RPL6 | 4.00 | 9.86E−05 |
| RPL19 | 3.98 | 0.0001 |
| RPL8 | 3.86 | 0.00015 |
| RPLP2 | 3.80 | 0.0002 |
| RPL34 | 3.63 | 0.0003 |
| RPL4 | 3.05 | 0.002 |
| RPL29 | 2.94 | 0.002 |
| RPL27A | 2.87 | 0.003 |
| RPL5 | 2.74 | 0.004 |
| RPL28 | 2.33 | 0.01 |
| RPL18A | 2.28 | 0.01 |
| RPL36AL | 1.70 | 0.048 |
| RPS18 | 4.96 | 3.71E−06 |
| RPS27A | 4.63 | 1.19E−05 |

TABLE 7-continued

Ribosomal Protein Gene Transcripts Up-regulated in Human Breast Cancers (Cancer Epithelia vs. Tumor Stroma).

| Gene Symbol | Fold-Increase | P-Value |
|---|---|---|
| RPS3A | 4.59 | 1.35E-05 |
| RPS6 | 4.47 | 2.04E-05 |
| RPS10 | 4.18 | 5.34E-05 |
| RPS19 | 4.17 | 5.49E-05 |
| RPS11 | 3.58 | 0.0004 |
| RPS2 | 3.36 | 0.0007 |
| RPS29 | 2.31 | 0.01 |

In addition, Table 8 illustrates that of the 10 chaperone proteins that were up-regulated during co-culture, 7 were significantly increased by >3.1-fold in human breast cancer cells in vivo. As such, 70% of the chaperone proteins increased during co-culture were also increased in human breast cancer cells. The proteins shown in Table 8 were all upregulated in MCF7-Fibroblast Co-cultures ($p<0.05$).

TABLE 8

Other Chaperone Gene Transcripts Up-regulated in Human Breast Cancers (Cancer Epithelia vs. Tumor Stroma).

| Gene Symbol | Fold-Increase | P-Value |
|---|---|---|
| HSP90AB1 | 4.93 | 4.03E-06 |
| HSPA5 | 3.89 | 0.0001 |
| HSP90AA1 | 3.76 | 0.0002 |
| HSPA4 | 3.75 | 0.0002 |
| HSPB1 | 3.27 | 0.001 |
| HSPH1 | 3.18 | 0.001 |
| HSPA8 | 3.11 | 0.002 |

Finally, Table 9 shows that of the 30 proteins associated with mRNA translation initiation, polypeptide elongation, and tRNA synthesis, 19 were significantly increased by >1.7-fold in human breast cancer cells in vivo. As a result, >60% of these proteins were also increased in human breast cancer cells.

TABLE 9

Transcripts of Genes Associated with mRNA Translation Initiation, Polypeptide Elongation, and tRNA Synthesis Are All Up-regulated in Human Breast Cancers (Cancer Epithelia vs. Tumor Stroma).

| Gene Symbol | Fold-Increase | P-Value |
|---|---|---|
| Translation initiation factors (required for mRNA binding to ribosomes) | | |
| EIF4H | 4.77 | 7.20E-06 |
| EIF3H | 4.70 | 9.25E-06 |
| EIF5 | 3.90 | 0.0001 |
| EIF3E | 3.57 | 0.0004 |
| EIF3A | 2.51 | 0.008 |
| EIF3B | 2.21 | 0.02 |
| Elongation factors (promote delivery of aminoacyl tRNAs to the ribosome) | | |
| EEF2 | 4.01 | 9.29E-05 |
| EEF1G | 3.71 | 0.0002 |
| TUFM | 3.38 | 0.0007 |
| EEF1A1 | 3.16 | 0.001 |
| EEF1D | 2.50 | 0.008 |
| Enzymes for tRNA Synthesis | | |
| IARS2 | 4.70 | 9.15E-06 |
| RTCB | 4.59 | 1.37E-05 |

TABLE 9-continued

Transcripts of Genes Associated with mRNA Translation Initiation, Polypeptide Elongation, and tRNA Synthesis Are All Up-regulated in Human Breast Cancers (Cancer Epithelia vs. Tumor Stroma).

| Gene Symbol | Fold-Increase | P-Value |
|---|---|---|
| MARS | 4.35 | 3.00E-05 |
| EPRS | 4.06 | 8.10E-05 |
| QARS | 3.73 | 0.0002 |
| DARS | 3.43 | 0.0006 |
| DTD1 | 1.78 | 0.04 |
| YARS | 1.72 | 0.046 |

Such a high concordance rate between i) in vitro proteomics data and ii) in vivo human breast cancer transcriptional mRNA data, validates the translational significance of the MCF7-fibroblast co-culture system, as a model for studying human breast cancer.

Figure 5:
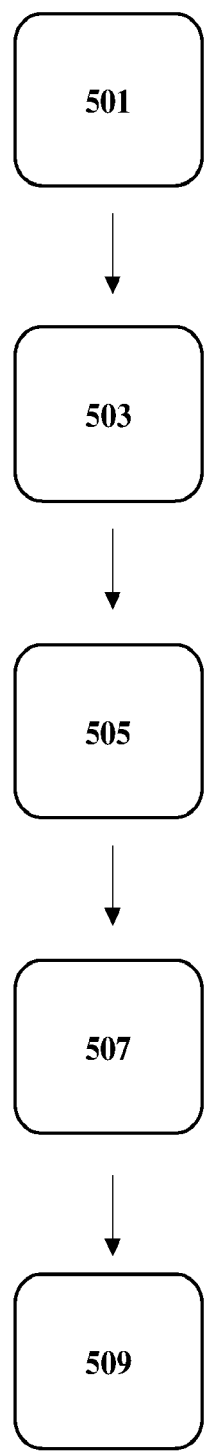
FIG. 5 illustrates a proteomics-based approach to the development of companion diagnostics for cancer, and in this embodiment, for predicting Tamoxifen resistance in breast cancer.

In view of the foregoing, new prognostic biomarkers and companion diagnostics have been established for predicting Tamoxifen-resistance, by exploiting proteomics data from MCF7-fibroblast co-cultures. The co-culture of MCF7 cells with fibroblasts induces a Tamoxifen-resistance phenotype. The proteomics data from MCF7-fibroblast co-cultures and publically available transcriptional profiling data from the tumors of breast cancer patients that were treated with Tamoxifen, but did not receive any chemotherapy, may be used to identify new potential biomarkers of Tamoxifen-resistance. FIG. 5 illustrates an approach for identifying prognostic biomarkers according to an embodiment of the present disclosure. Under this approach, an unbiased proteomics analysis 501 may be performed on a co-culture, such as the MCF7-fibroblast co-culture described herein. Mitochondrial marker proteins, including mitochondrial ribosomal proteins, mito-chaperones, and OXPHOS complex I-V components, are identified 503. Proteins up-regulated, preferably by at least a 1.5-fold increase, are then identified 505. Next, bioinformatics analysis may be used to cross-reference the identified up-regulated mitochondrial marker proteins with existing transcriptional gene profiling and outcome data, resulting in the generation of prognostic gene signatures 507. A prognostic gene signature may be used as a predictor of the outcome (e.g., treatment failure, drug resistance, etc.), as well as identifying new targets for drug therapy 509. The demonstrative embodiment relates to companion diagnostics for predicting Tamoxifen resistance in breast cancer. It should be appreciated that the present approach may be used for other cancer types and other modes of treatment failure.

As a demonstrative example of the approach, the data used were from high-risk patients that were lymph-node positive at diagnosis, and in particular, on the luminal A subtype, which represents the most common form of ER(+) breast cancers (N=152 patients). The results of this analysis are shown in Table 10, below. In this context, seven distinct mitochondrial genes, represented by 9 different gene probes, showed significant prognostic value, and were able to predict tumor recurrence. RFS in Table 10 is recurrence-free survival.

TABLE 10

Prognostic Value of Mitochondrial Markers Induced During Metabolic Symbiosis (MCF7-Fibro) for Tumor Recurrence.

| Gene Probe ID | Symbol | Hazard-Ratio (RFS) | Log-Rank Test |
|---|---|---|---|
| 211662_s_at | VDAC2 | 3.96 | 6.7e-07 |
| 200807_s_at | HSPD1 | 3.46 | 1.3e-05 |

TABLE 10-continued

Prognostic Value of Mitochondrial Markers Induced During
Metabolic Symbiosis (MCF7-Fibro) for Tumor Recurrence.

| Gene Probe ID | Symbol | Hazard-Ratio (RFS) | Log-Rank Test |
|---|---|---|---|
| 200806_s_at | HSPD1 | 2.34 | 0.005 |
| 203633_at | CPT1A | 2.86 | 0.01 |
| 203634_s_at | CPT1A | 2.32 | 0.025 |
| 202698_x_at | COX4I1 | 2.19 | 0.038 |
| 211971_s_at | LRPPRC | 2.05 | 0.01 |
| 200657_at | SLC25A5 | 2.40 | 0.002 |
| 221235_s_at | TRAP1 | 1.77 | 0.048 |

In order to increase the prognostic power of these individual mitochondrial biomarkers, the top 3 most promising biomarkers, in terms of hazard-ratio, were selected and investigated as a potential mitochondrial gene signature. It should be appreciated that more or less may be selected in other embodiments, depending on the data and subsequent validation. This new Mito-Signature contains only 3 key genes (HSPD1, VDAC2, CPT1A). Table 11, below, shows the prognostic value of this 3-gene signature for predicting treatment failure due to tumor recurrence.

TABLE 11

Combined Prognostic Value of 3-Gene Mitochondrial Signature
for Predicting Treatment Failure due to Tumor Recurrence.

| Gene Probe ID | Symbol | Hazard-Ratio (RFS) | Log-Rank Test |
|---|---|---|---|
| 211662_s_at | VDAC2 | 3.96 | 6.7e−07 |
| 200807_s_at | HSPD1 | 3.46 | 1.3e−05 |
| 203633_at | CPT1A | 2.86 | 0.01 |
| Combined | | 5.52 | 7.3e−10 |

The 3-gene mitochondrial signature also has prognostic value for predicting treatment failure due to distant metastasis, as shown in Table 12, below. The acronym DMFS refers to distant metastasis-free survival.

TABLE 12

Combined Prognostic Value of 3-Gene Mitochondrial Signature
for Predicting Treatment Failure due to Distant-Metastasis.

| Gene Probe ID | Symbol | Hazard-Ratio (DMFS) | Log-Rank Test |
|---|---|---|---|
| 211662_s_at | VDAC2 | 3.11 | 0.0004 |
| 200807_s_at | HSPD1 | 3.50 | 9.7e−05 |
| 203633_at | CPT1A | 2.79 | 0.026 |
| Combined | | 5.51 | 8.1e−07 |

It should be appreciated that establishing that a protein has prognostic value for predicting a particular outcome (e.g., Tamoxifen resistance) requires multivariate survival analysis (e.g., using Kaplan-Meier curves), hazard-ratio calculation, and p-values (e.g., using the log-rank test), as are known in the art. The Kaplan-Meier estimator is used in the art to estimate the survival function. The visual representation of the survival function, called a Kaplan-Meier curve, illustrates the probability of an event (for example, survival) over a certain time interval.

Figure 6A:
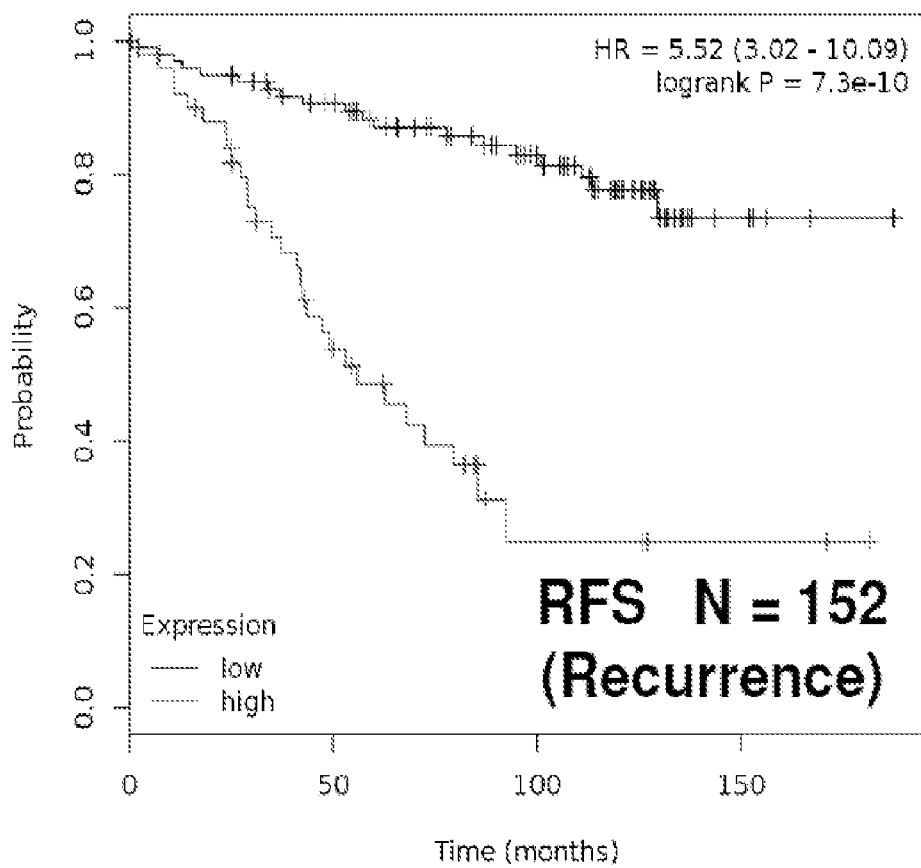
FIGS. 6A and 6B show Kaplan-Meier curves using the 3-gene mitochondrial signature for LN(+) Luminal A patients treated with Tamoxifen.
Figure 6B:
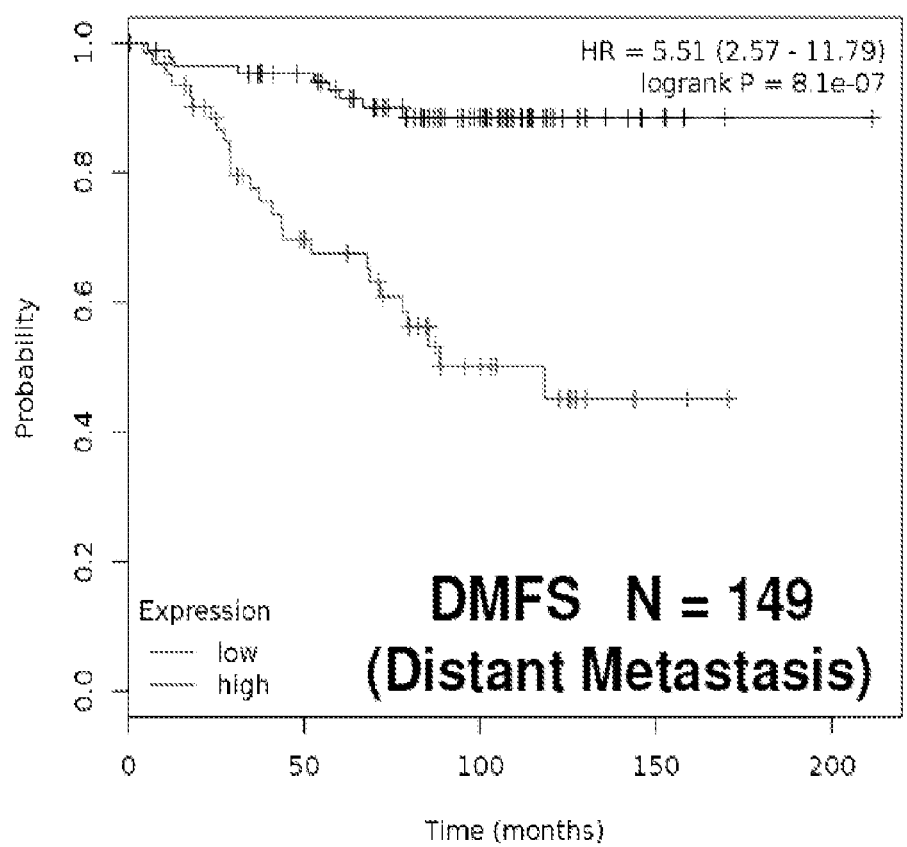

Kaplan-Meier curves for the 3-gene signature of HSPD1, VDAC2, and CPT1A are shown in FIGS. 6A through 13B. The 3-gene mitochondrial signature of HSPD1, VDAC2, and CPT1A (a "Mito-Signature") effectively predicts recurrence and distant metastasis in high-risk ER(+) breast cancer patients. The Kaplan-Meier curves in FIGS. 6A and 6B show that the Mito-Signature of HSPD1, VDAC2, and CPT1A predicts tumor recurrence (N=152 patients; p=7.3e-10), and distant metastasis (N=149 patients; p=8.1e-07), respectively, in LN(+) luminal A patients treated with Tamoxifen therapy, indicative of treatment failure and Tamoxifen-resistance. Patients with high-expression levels of the Mito-Signature showed a >5-fold increase in recurrence and distant metastasis, while being treated with hormonal therapy.

Figure 7A:
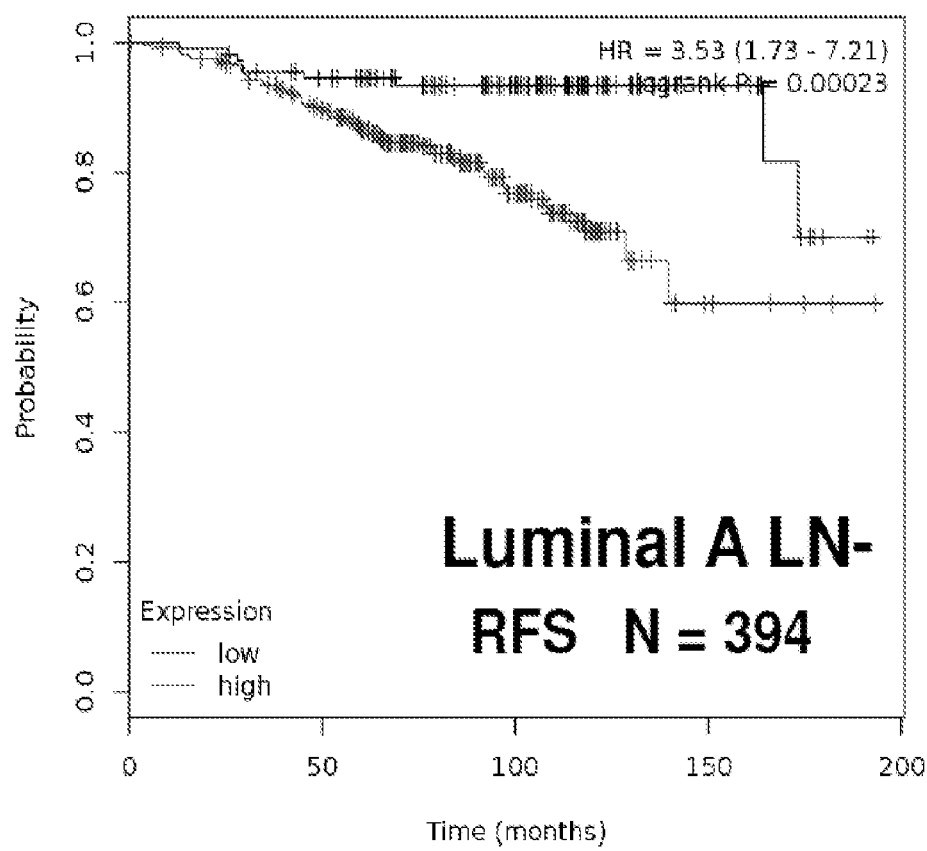
FIGS. 7A and 7B show Kaplan-Meier curves using the 3-gene mitochondrial signature for LN(−) Luminal A patients and Luminal B patients treated with hormonal therapy.
Figure 7B:
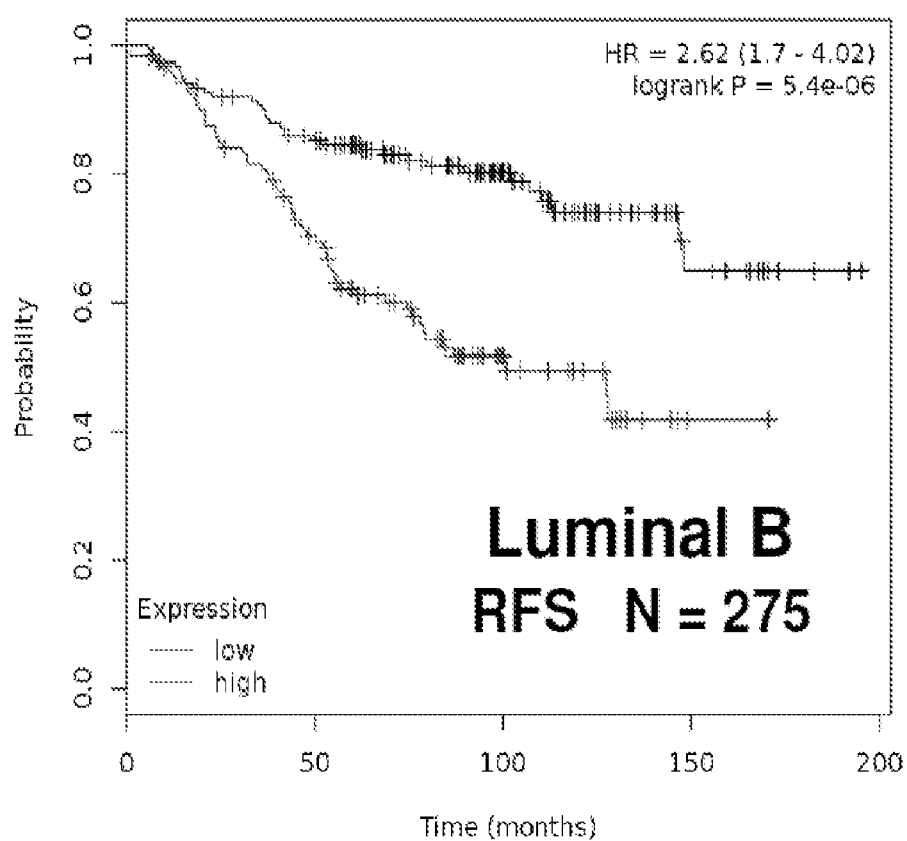

FIGS. 7A and 7B are Kaplan-Meier curves that show the Mito-Signature's predictive value in Luminal A (LN-negative) and Luminal B breast cancer patients, who were treated with hormonal therapy. Tumor recurrence was the event. FIG. 7A relates to Luminal A/LN-negative (N=394 patients; p=0.00023), and FIG. 7B relates to Luminal B (N=275 patients; p=5.4e-06). Patients with high-expression levels of the Mito-Signature showed a clear increase in recurrence, while being treated with hormonal therapy.

Figure 8A:
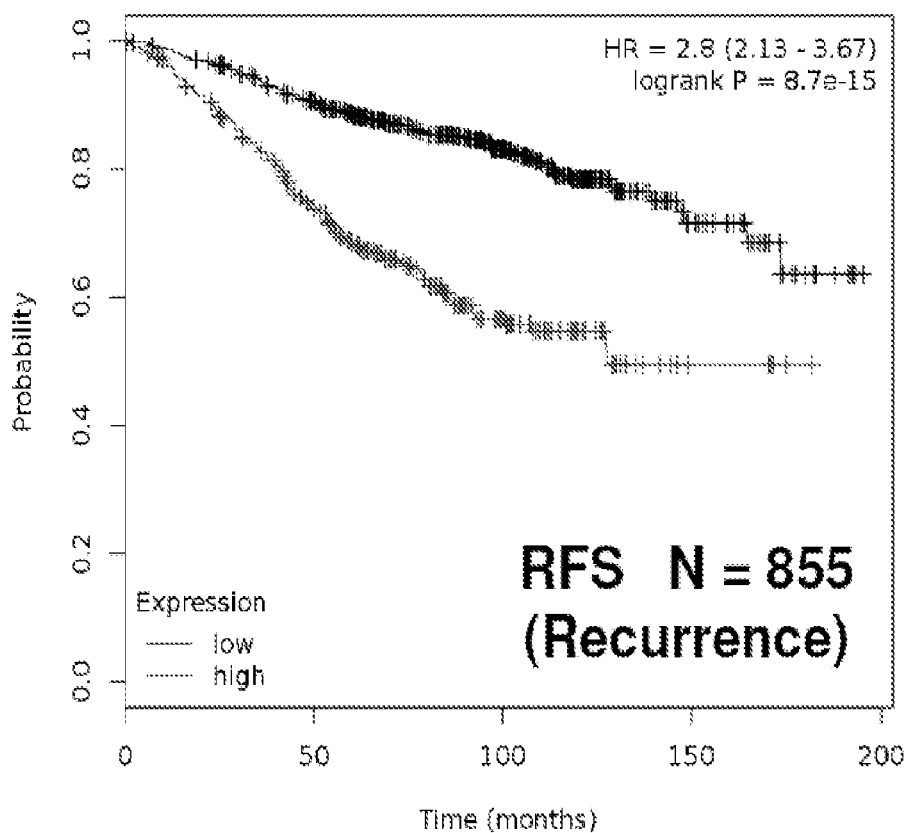
FIGS. 8A and 8B show Kaplan-Meier curves using the 3-gene mitochondrial signature for ER(+) breast cancer patients treated with hormonal therapy.
Figure 8B:
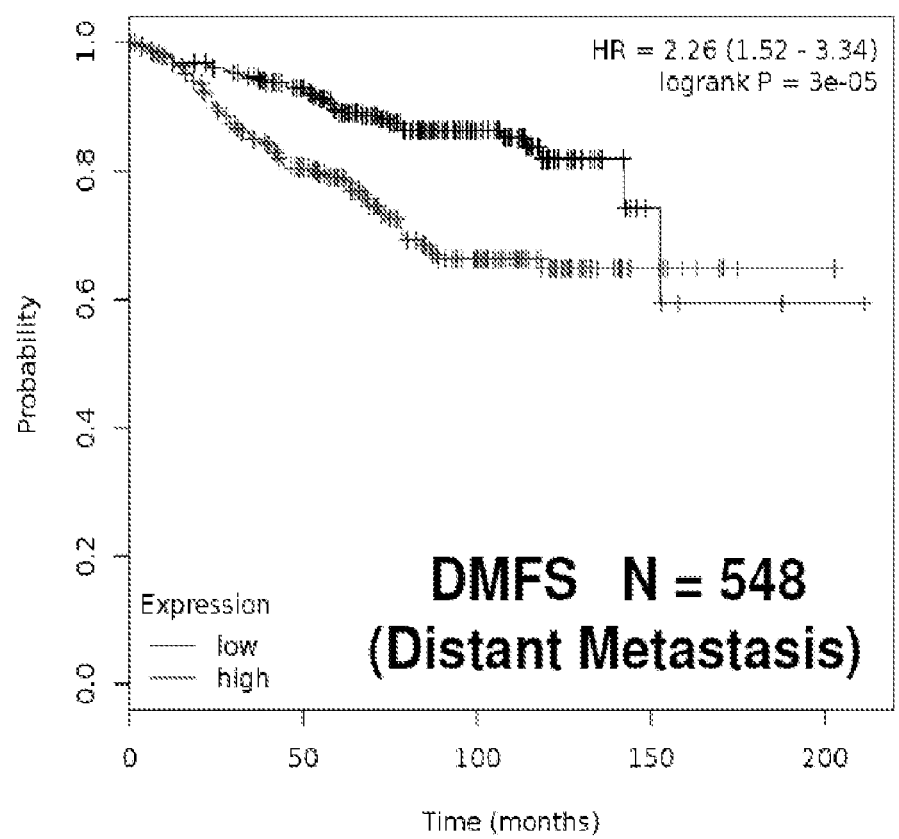

FIGS. 8A and 8B show Kaplan-Meier curves using the 3-gene mitochondrial signature of HSPD1, VDAC2, and CPT1A, for ER(+) breast cancer patients treated with hormonal therapy, tumor recurrence being the event. FIG. 8A is the Kaplan-Meier curve for tumor recurrence, and FIG. 8B is the Kaplan-Meier curve for distant metastasis. These patients were not sub-divided into luminal A/B subgroups and were not sub-divided by lymph-node status. Note that the Mito-Signature of HSPD1, VDAC2, and CPT1A, effectively predicts tumor recurrence (Left; N=855 patients) and distant metastasis (Right; N=548 patients). Patients with high-expression levels of the Mito-Signature showed a near 3-fold increase in recurrence (p=8.7e-15) and a >2-fold increase in distant metastasis (p=3e-05), while being treated with hormonal therapy.

Figure 9A:
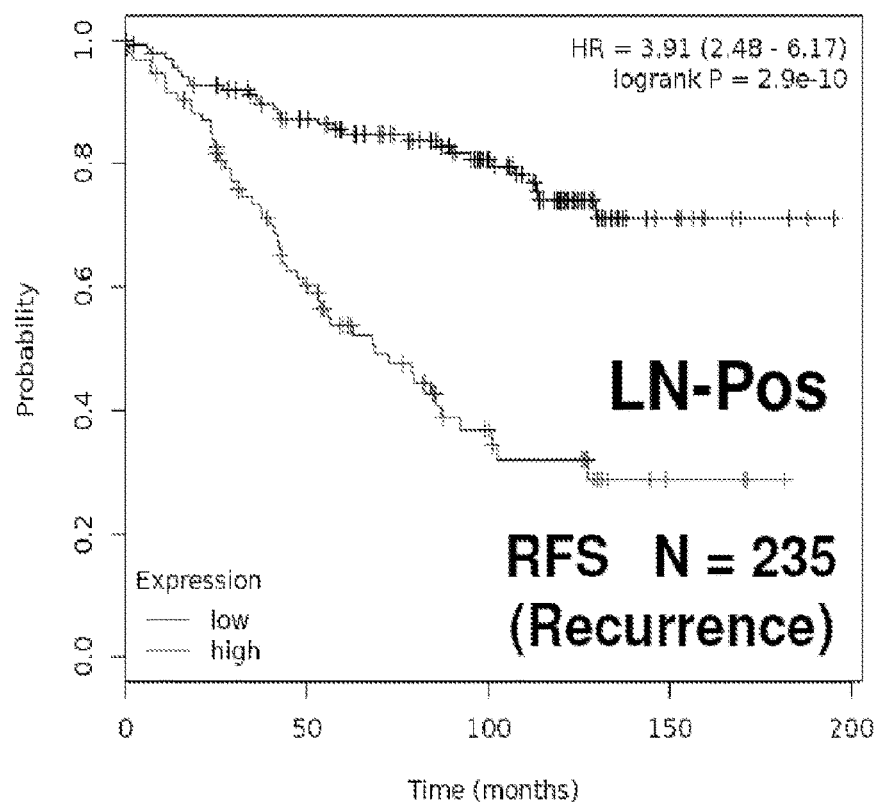
FIGS. 9A and 9B are Kaplan-Meier curves using the 3-gene Mito-Signature for ER(+) breast cancer patients in sub-groups by lymph node status, treated with hormonal therapy.
Figure 9B:
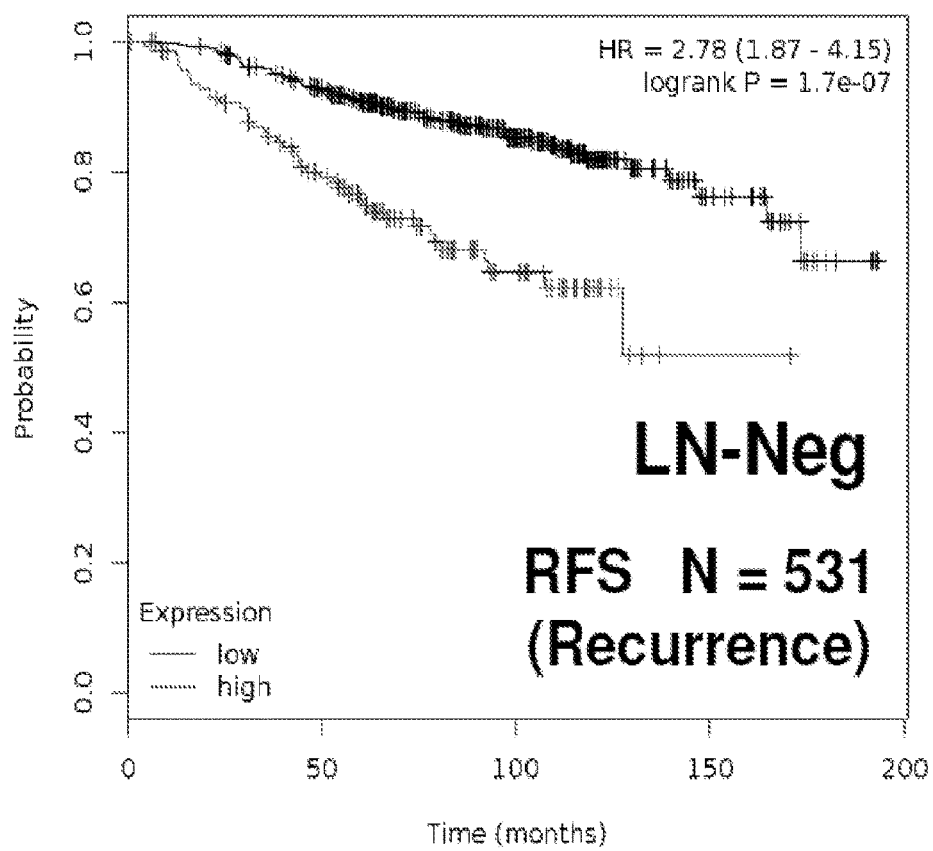

FIGS. 9A and 9B are Kaplan-Meier curves using the 3-gene Mito-Signature for ER(+) breast cancer patients in sub-groups by lymph node status, treated with hormonal therapy. Tumor recurrence was the event. FIG. 9A relates to the lymph node positive (LN-Pos; N=235 patients) subgroup, and FIG. 9B relates to the lymph node negative (LN-Neg; N-531 patients) sub-group. These patients were not sub-divided into luminal A/B subgroups. LN-positive patients with high-expression levels of the Mito-Signature showed a near 4-fold increase in recurrence, while being treated with hormonal therapy (p=2.9 e-10). Similar results were observed in LN-negative patients, with a near 3-fold increase in recurrence (p=1.7e-07).

Figure 10:
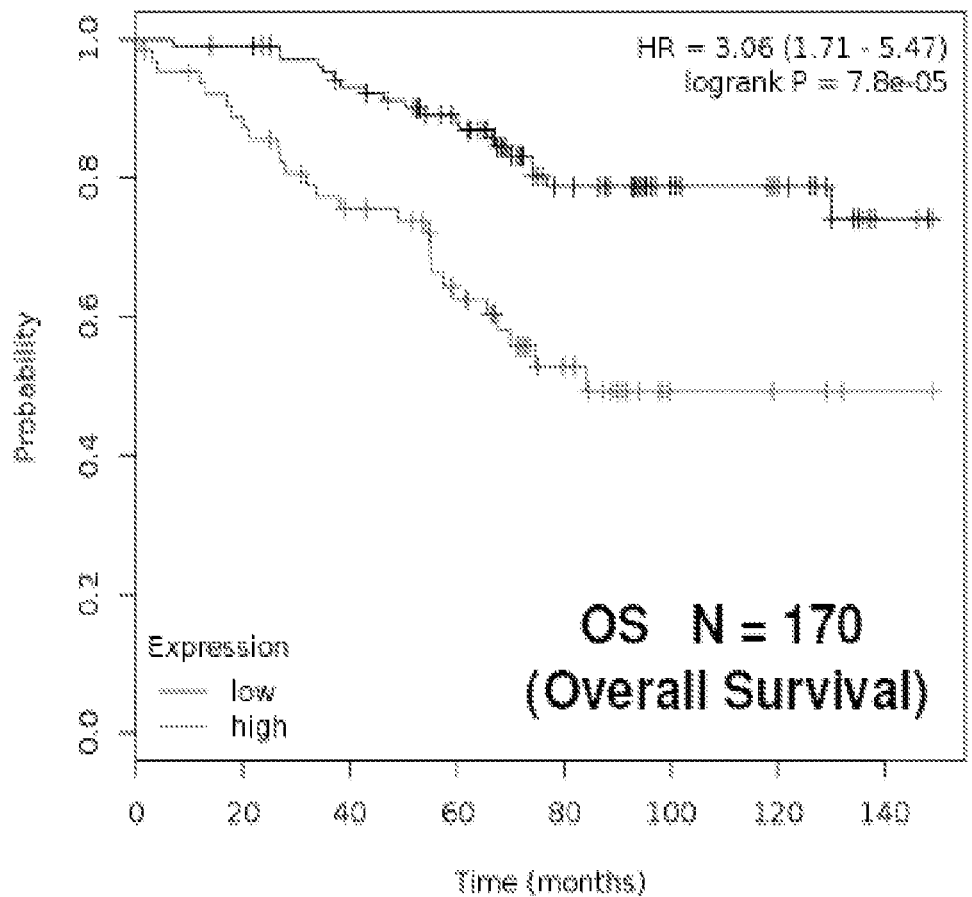
FIG. 10 is a Kaplan-Meier curve using the 3-gene Mito-Signature on ER(+) breast cancer patients treated with hormonal therapy.

FIG. 10 is a Kaplan-Meier curve using the 3-gene Mito-Signature on ER(+) breast cancer patients treated with hormonal therapy, using overall survival as the event. Patients with high-expression levels of the Mito-Signature showed a >3-fold reduction in long-term survival (N=170 patients; p=7.8e-05).

Figure 11A:
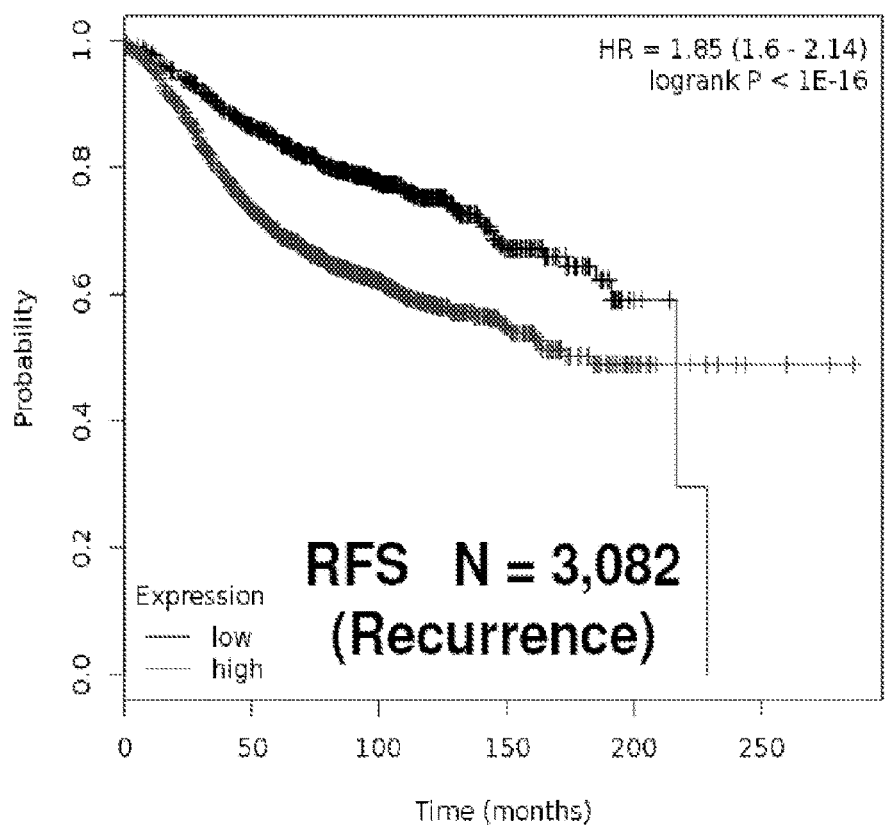
FIGS. 11A and 11B are Kaplan-Meier curves using the 3-gene Mito-Signature on ER(+) breast cancer patients, independent of treatment, with tumor recurrence and metastasis, respectively, being the events.
Figure 11B:
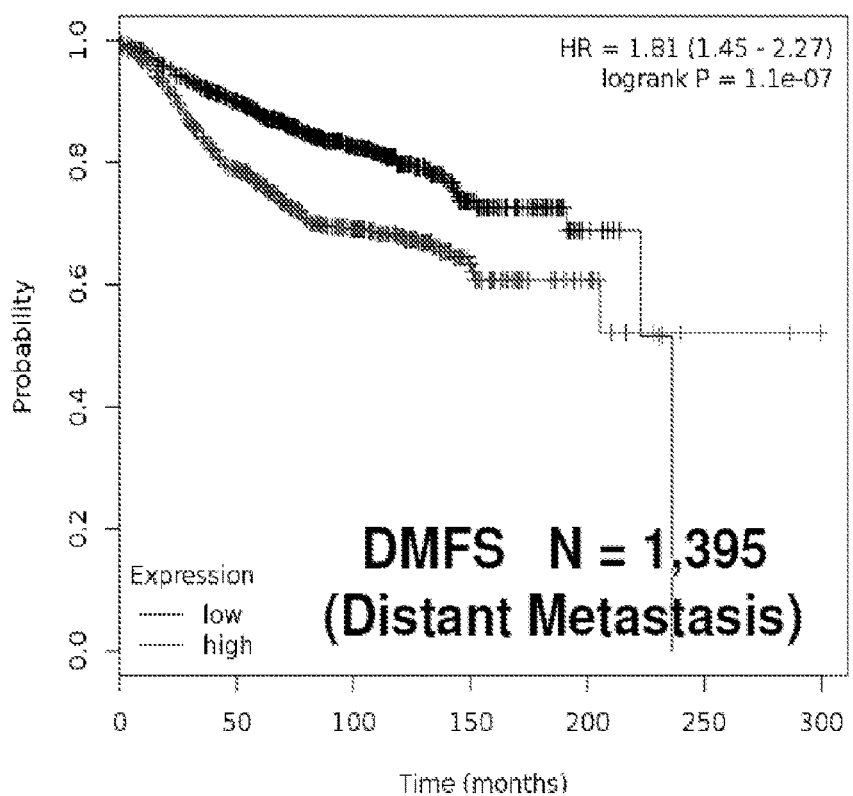

FIGS. 11A and 11B are Kaplan-Meier curves using the 3-gene Mito-Signature on ER(+) breast cancer patients, independent of treatment, with tumor recurrence and metastasis, respectively, being the events. Patients with high-expression levels of the Mito-Signature showed near 2-fold increases in recurrence from FIG. 11A (N=3,082; p<1e-16), and distant metastasis from FIG. 11B (N=1,395; p=1.1e-07).

Figure 12A:
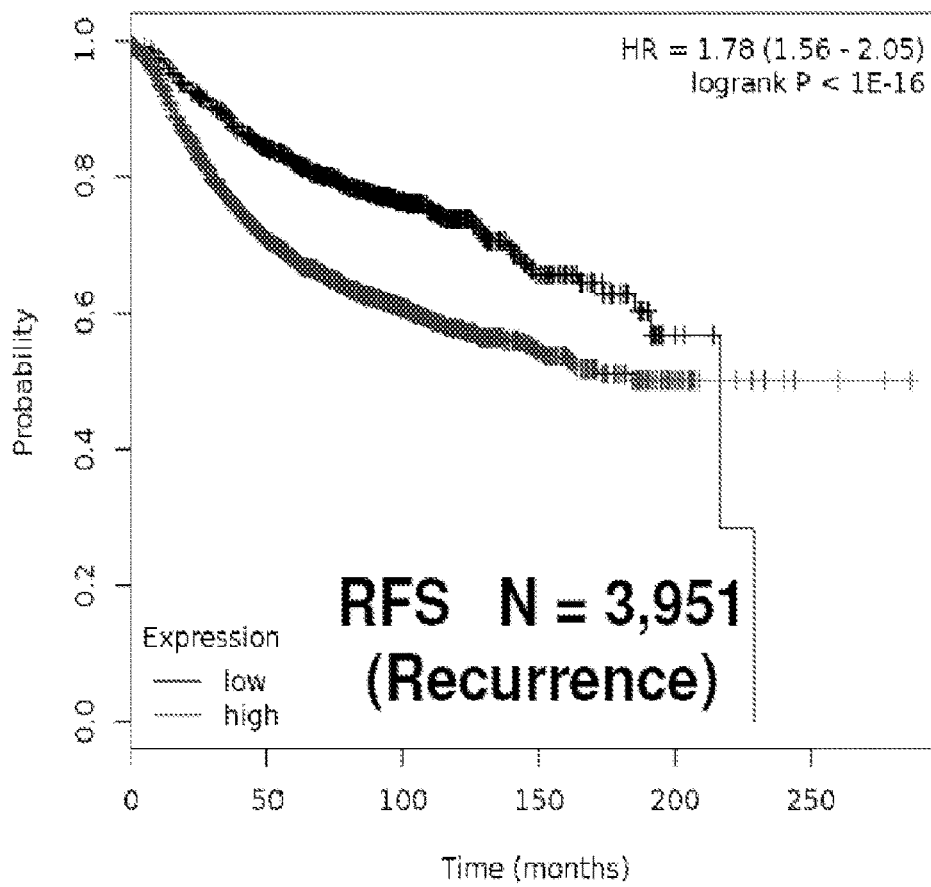
FIGS. 12A and 12B are Kaplan-Meier curves using the 3-gene Mito-Signature on a large data set of breast cancer patients, independent of treatment, with tumor recurrence and metastasis, respectively, being the events.
Figure 12B:
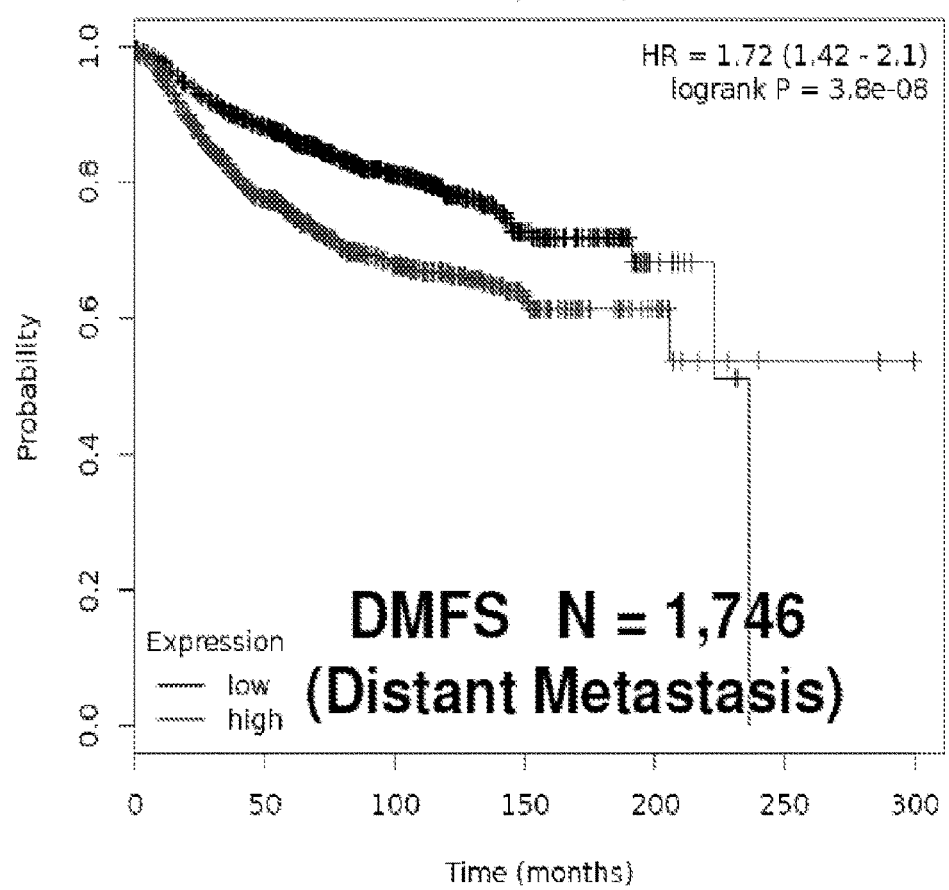

FIGS. 12A and 12B are Kaplan-Meier curves using the 3-gene Mito-Signature on a large data set of breast cancer patients, independent of treatment, with tumor recurrence and metastasis, respectively, being the events. Patients with high-expression levels of the Mito-Signature showed near 2-fold increases in recurrence (N=3,951; p<1e-16) and distant metastasis (N=1,746; p=3.8e-08).

Figure 13A:
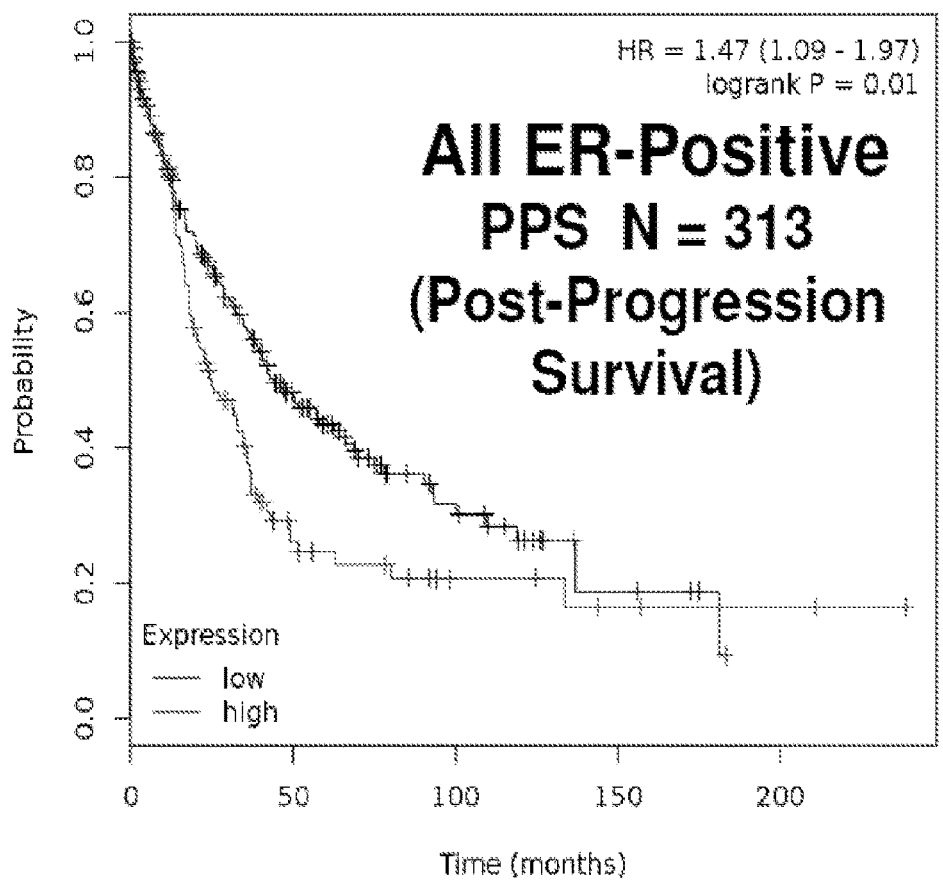
FIGS. 13A and 13B are Kaplan-Meier curves using the 3-gene Mito-Signature on ER(+) breast cancer patients and all breast cancer patients, respectively, using post-progression survival as the event.
Figure 13B:
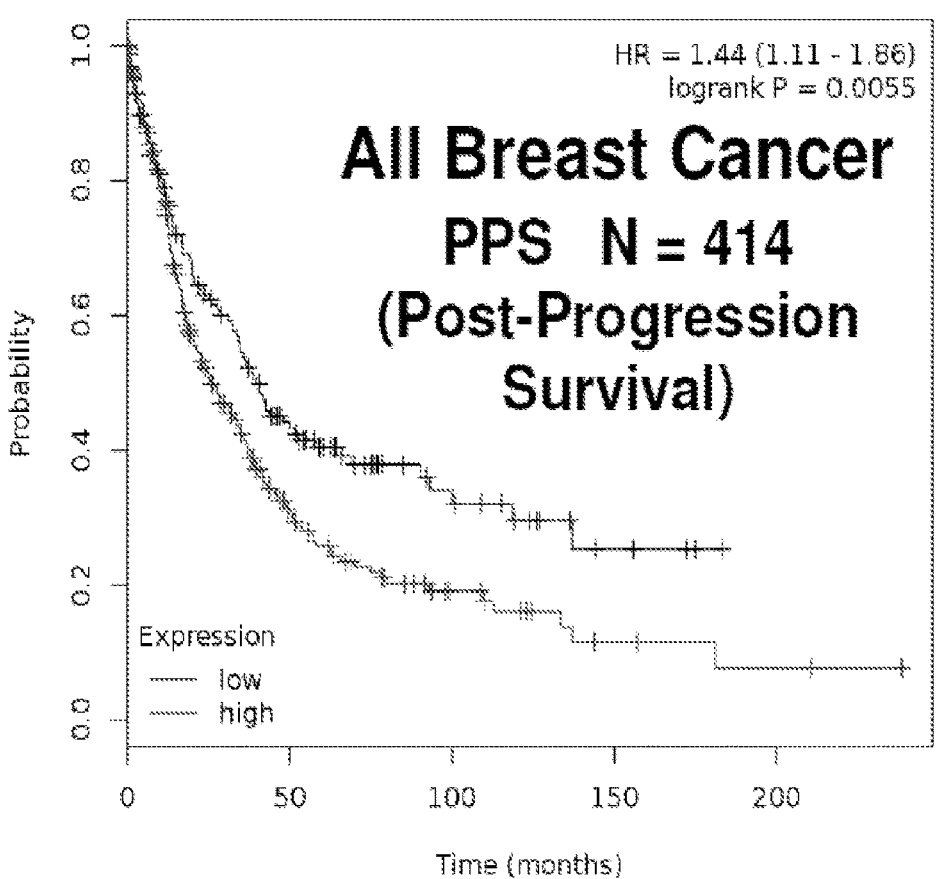

FIGS. 13A and 13B are Kaplan-Meier curves using the 3-gene Mito-Signature on ER(+) breast cancer patients and all breast cancer patients, respectively, using post-progression survival as the event. Patients with high-expression levels of the Mito-Signature showed near 1.5-fold reductions in post-progression survival. Left, ER(+) (N=313 patients; p=0.01). Right, all breast cancer (N=414 patients; p=0.0055).

Importantly, the 3-gene Mito-Signature described above yielded a significantly improved hazard-ratio for tumor recurrence of 5.52 (p=7.3e-10). It was also highly predictive for distant metastasis, in the same group of patients (HR=5.51; p=8.1e-07), as evident in FIGS. 6A and 6B. Similar results were obtained in Luminal A LN-negative patients and Luminal B patients, as seen in FIGS. 7A and 7B.

The 3-gene mitochondrial gene signature also showed prognostic value in a larger group of ER(+) patients (N=855), that received hormonal therapy, but not chemotherapy. This group of patients was not segregated into luminal A and luminal B subtypes. FIGS. 8A and 8B show the results of this Kaplan-Meier curves for relapse-free survival (HR=2.80; p=8.7e-15). Similar results were also obtained distant metastasis-free survival (HR=2.26; p=3e-05; N=548 patients). This mitochondrial signature was also effective if the ER(+) patient population was divided into LN(+) and LN(−) groups, as seen in FIGS. 9A and 9B.

Next, the 3-gene Mito-Signature demonstrated prognostic value in predicting overall survival. FIG. 10 shows that it was also highly predictive of overall survival during hormonal therapy (HR=3.06; p=7.8e-05; N=170 patients). Moreover, FIGS. 11A and 11B show that this Mito-Signature was also effective in all ER(+) breast cancer patients in predicting tumor recurrence (N=3,082), as well as distant metastasis (N=1,395). Similar results were obtained using data from all breast cancer patients, for recurrence (N=3,951) and metastasis (N=1,746), as well as for post-progression survival (FIGS. 12A, 12B, 13A, and 13B). Thus, this mitochondrial-based gene signature represents an important new prognostic tool for predicting patient outcomes, in a wide variety of different breast cancer patients, but especially in ER(+) patients treated with hormonal therapies.

Markers of fibrosis and glycolysis were up-regulated in MCF7-fibroblast co-cultures, consistent with the onset of oxidative stress. During the co-culture of fibroblasts with cancer cells, their phenotype was observed to drastically change. These changes are related to the induction of various biological processes related oxidative stress, and are consistent with a more myo-fibroblastic phenotype. These phenotypic changes include increased expression of cytoskeletal elements and glycolytic enzymes, as well as the elevation of markers of autophagy and senescence. These biological processes are evident in the proteomics data.

Table 11, below, illustrates that during MCF7-fibroblast co-cultures, many known markers of fibrosis and oxidative stress are actually increased. These changes include the up-regulation of 32 cytoskeletal and extracellular matrix proteins, 11 glycolytic enzymes, 4 lysosomal/autophagy markers and 2 markers of the senescence-associated secretory phenotype, known as SASP. These findings are also consistent with the IPA analysis results, shown in FIG. 4. Therefore, the present approach also provides interesting new stromal targets for further validation in future studies.

TABLE 10

Proteomics Analysis: Stromal CAF Markers are Up-regulated in MCF7-Fibroblast Co- Cultures.

| Gene Symbol | Description | Fold-Increase |
|---|---|---|
| Glycolytic Enzymes | | |
| PKM | Pyruvate kinase | Infinity |
| LDHA | L-Lactate dehydrogenase A | 426.16 |
| PGD | 6-Phosphogluconate dehydrogenase, decarboxylating | 13.59 |
| ENO1 | Alpha-Enolase | 11.60 |
| ALDOA | Fructose-bisphosphate aldolase | 7.14 |
| PGI | Glucose-6-phosphate isomerase | 5.02 |
| PFK | 6-Phosphofructokinase | 4.14 |
| PGK1 | Phosphoglycerate kinase 1 | 4.38 |
| TPI1 | Triosephosphate isomerase 1 | 2.66 |
| G6PD | Glucose-6-phosphate 1-dehydrogenase | 2.28 |
| Cytoskeletal and Extracellular Matrix Proteins | | |
| MYH9 | Myosin Heavy Chain 9 | 226.32 |
| COL4A1 | Collagen Type IV Alpha 1 Chain | 211.46 |
| CTTN | Cortactin | 202.50 |
| DNHD1 | Dynein heavy chain domain-containing protein 1 | 195.80 |
| NEFL | Neurofilament light polypeptide | 124.55 |
| FLNA | Filamin-A | 60.54 |
| KIF5C | Kinesin heavy chain isoform 5C | 60.34 |
| TLN1 | Talin-1 | 33.25 |
| S100P | S100 Calcium Binding Protein P | 21.23 |
| SPTAN1 | Spectrin alpha chain, non-erythrocytic 1 | 11.78 |
| MYH11 | Myosin Heavy Chain 11 | 8.99 |
| DYNC1H1 | Cytoplasmic dynein 1 heavy chain 1 | 8.51 |
| COL1A1 | Collagen Type I Alpha 1 Chain | 7.38 |
| CFL1 | Cofilin-1 | 6.36 |
| MYO18B | Myosin XVIIIB | 6.11 |
| PLEC1 | Plectin 1, intermediate filament binding protein | 5.48 |
| SRRM2 | Serine/arginine repetitive matrix protein 2 | 5.18 |
| S100A16 | S100 Calcium Binding Protein A16 | 4.87 |
| SRRM1 | Serine/arginine repetitive matrix protein 1 | 4.77 |
| ACTN2 | Alpha-actinin-2 | 4.31 |
| MAP4 | Microtubule-associated protein | 4.22 |
| DNM2 | Dynamin-2 | 4.10 |
| ARPC1B | Actin related protein 2/3 complex, subunit 1B | 3.43 |
| MACF1 | Microtubule-actin cross-linking factor 1 | 3.26 |
| VCL | Vinculin | 2.66 |
| TPM4 | Tropomyosin alpha-4 | 2.65 |
| ANKRD12 | Ankyrin repeat domain-containing protein 12 | 2.58 |
| VIL2 | Villin 2 (Ezrin) | 2.57 |
| DYNC1LI2 | Cytoplasmic dynein 1 light intermediate chain 2 | 2.42 |
| VIM | Vimentin | 2.37 |
| NEFM | Neurofilament medium polypeptide | 2.35 |
| TUBB3 | Tubulin beta-3 | 2.35 |
| Senescence and Senescence-Associated Secretory Phenotype | | |
| HMGB2 | High mobility group protein B2 | 64.01 |
| HMGB21 | High mobility group protein B1 | 4.00 |
| Autophagy/Lysosomal Markers | | |
| ATP6V1E1 | ATPase, H+transporting, lysosomal, V1 subunit E1 | 2.60 |
| ATP6V1A | V-type proton ATPase catalytic subunit A | 2.56 |
| CTSD | Cathepsin D | 2.08 |
| CTSZ | Cathepsin Z | 2.07 |

The relevance of MCF7-fibroblast co-cultures for drug development has been validated using FDA-approved antibiotics that target mitochondria. Forty-five mitochondrial proteins were significantly increased during the co-culture of stromal fibroblasts, with MCF7 cancer cells. This is consistent with studies employing the vital fluorescent dye MitoTracker, showing that mitochondrial mass is dramatically increased during MCF7-fibroblasts co-cultures. This may also have implications for drug sensitivity to mitochondrial inhibitors, especially those targeting mitochondrial biogenesis.

Figure 14A:
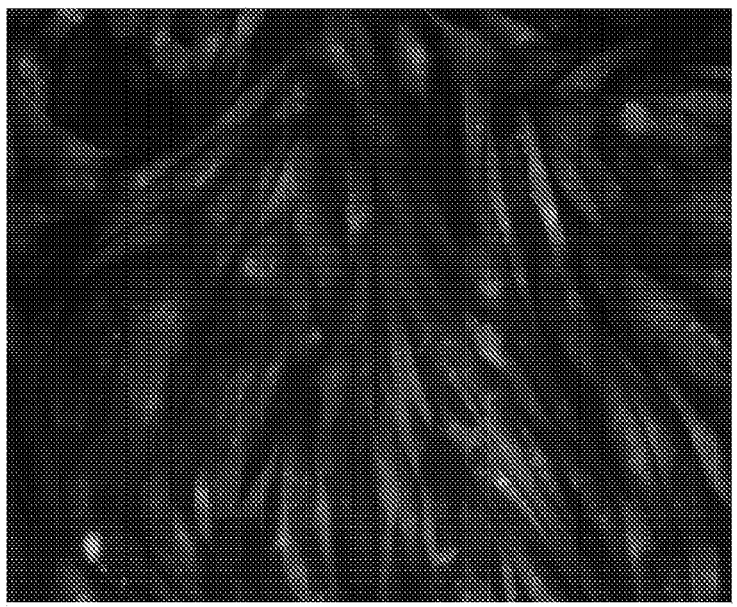
FIGS. 14A and 14B are representative images of hTERT-fibroblasts and MCF7 cells, respectively, expressing fluorescent proteins.
Figure 14B:
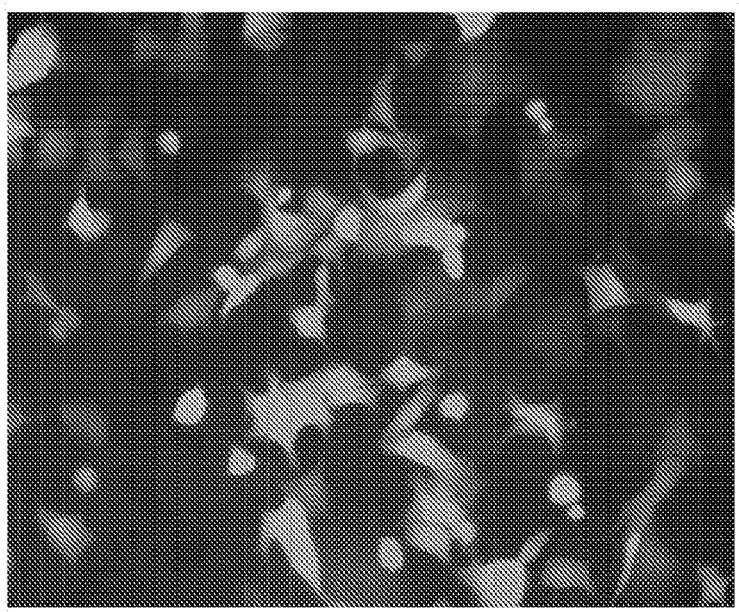

To directly test this hypothesis, a new assay system may be used to monitor the sensitivity of cancer cells to drug treatment, in the presence or absence of fibroblasts. For this purpose, hTERT-BJ1-fibroblasts expressing RFP (red fluorescent protein) and MCF7 cells expressing GFP (green fluorescent protein) were generated. Representative images of these mono-cultures are shown in FIGS. 14A (hTERT-BJ1-RFP) and 14B (MCF7-GFP). The hTERT-BJ1-fibroblasts expressing RFP and MCF7 cells expressing GFP were generated by lentiviral transduction. RFP, red fluorescent protein; GFP, green fluorescent protein.

Two FDA-approved antibiotics (Doxycycline and Azithromycin) were used as positive controls for this assay system. These antibiotics have been shown to act as inhibitors of mitochondrial biogenesis, because of the long-standing evolutionary relationship between mitochondria and bacteria. Doxycycline and Azithromycin both inhibit mitochondrial protein translation, as off-target "side-effects" of the compounds.

Figure 15:
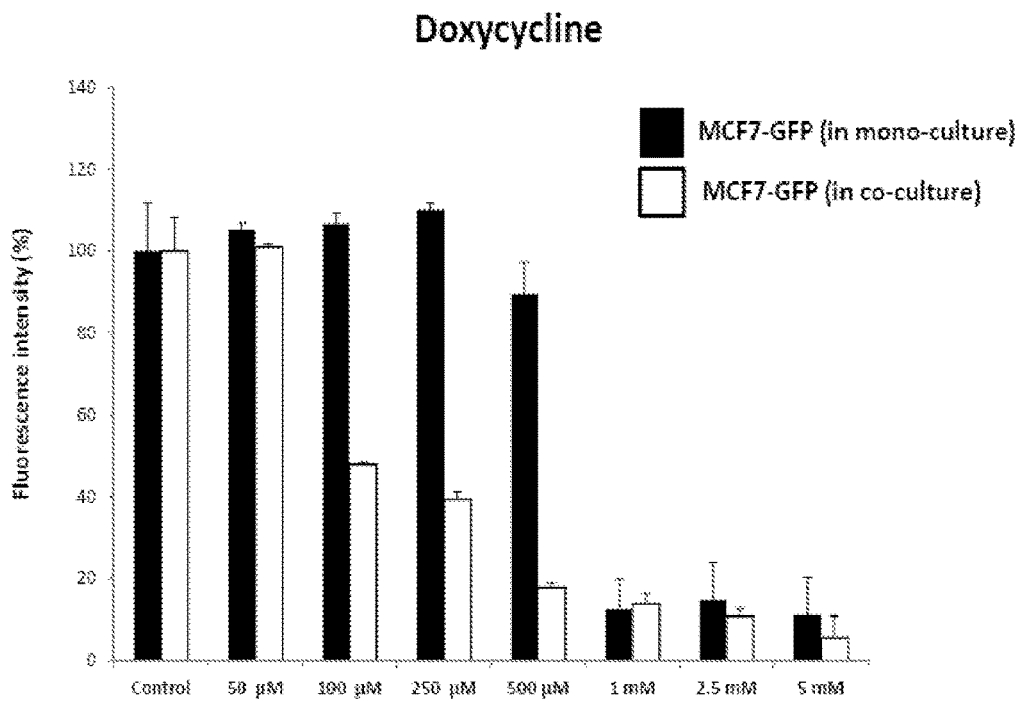
FIG. 15 shows the fluorescence intensity of MCF7-GFP in mono-culture and co-culture, at different concentrations of Doxycycline.

FIG. 15 shows the fluorescence intensity of MCF7-GFP in mono-culture and co-culture, at different concentrations of Doxycycline, and shows that Doxycycline preferentially targets MCF7-GFP cells, during co-culture with fibroblasts. Mono-cultures of MCF7-GFP cells are quantitatively more resistant to the killing effects of Doxycycline, as the concentration of Doxycycline is progressively increased from 50 µM to 5 mM. At 500 µM Doxycycline, MCF7-GFP cells in co-culture are ~5-fold more sensitive than those in mono-cultures. As predicted, Doxycycline preferentially targeted MCF7-GFP cells, during their co-culture with fibroblasts, as directly compared with MCF-GFP mono-cultures. Quantitation of cellular GFP fluorescence was performed using a plate-reader, at the appropriate wavelength (See Materials and Methods). At 500 µM Doxycycline, MCF7-GFP cells in co-culture were ~5-fold more sensitive, than those in mono-cultures. However, the increased sensitivity of MCF7-GFP cells in co-culture was first observed at 100 µM, but not at 50 µM. Doxycycline also begins to inhibit overall protein synthesis in mammalian cells, in the range of 100 µM to 1 mM. However, this effect is likely secondary to mitochondrial ATP-depletion (IC-50=50 µM). Therefore, Doxycycline may effectively target both "mito-stemness" and "ribo-stemness" features, by inhibiting both i) mitochondrial protein synthesis and ii) overall protein synthesis.

Representative images of these MCF7-fibroblast co-cultures and their differential sensitivity to Doxycycline are shown in FIGS. 16A-16D, showing the control, 250 µM, 500 µM, and 1 mM, respectively. Note the progressive reductions in GFP-fluorescence.

Figure 17:
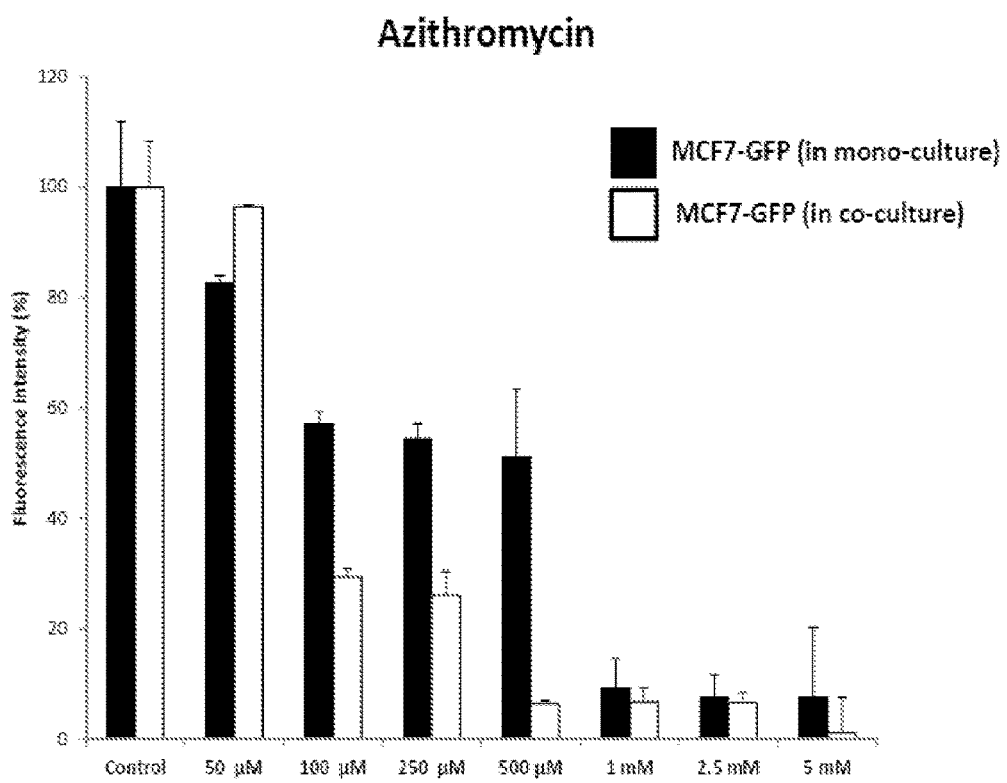
FIG. 17 shows the fluorescence intensity of MCF7-GFP in mono-culture and co-culture, at different concentrations of Azithromycin.
Figure 16A:
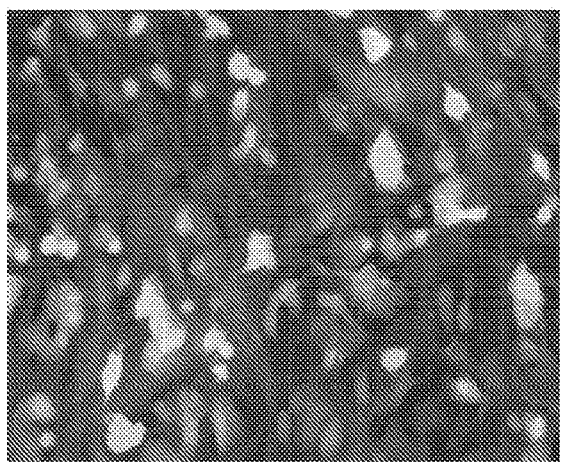
FIGS. 16A-16D show representative images of MCF7-fibroblast co-cultures and their differential sensitivity to Doxycycline.
Figure 16B:
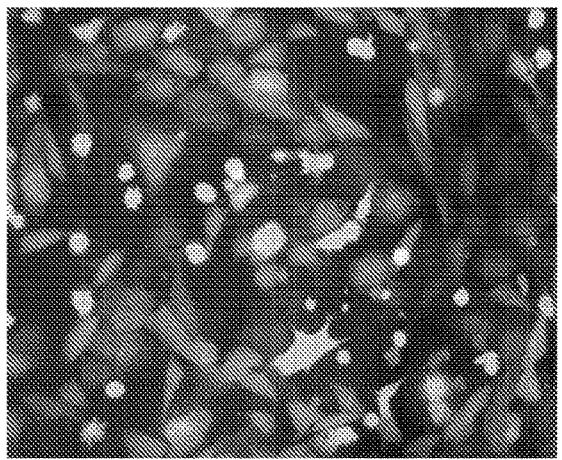
Figure 16C:
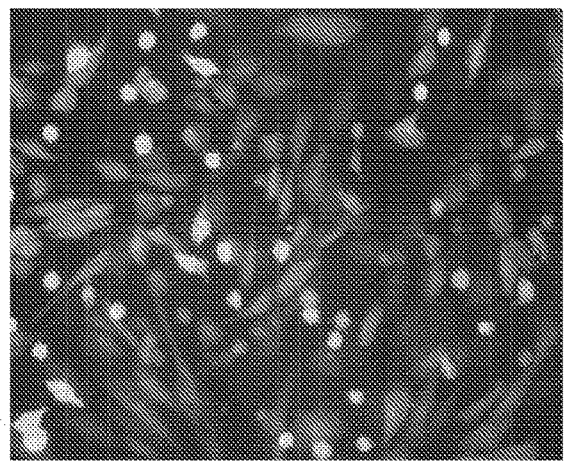
Figure 16D:

Quantitatively similar results were obtained with Azithromycin, another well-established inhibitor of mitochondrial biogenesis. FIG. 17 shows the fluorescence intensity of MCF7-GFP in mono-culture and co-culture, at different concentrations of Azithromycin. Mono-cultures of MCF7-GFP cells are quantitatively more resistant to the killing effects of Azithromycin, as the concentration of Azithromycin is progressively increased, from 50 µM to 5 mM. At 500 µM Azithromycin, MCF7-GFP cells in co-culture are ~8-fold more sensitive, than those in mono-cultures.

These pharmacological data (representing enhanced sensitivity to mitochondrial protein translation inhibitors) are consistent with the increases in mitochondrial biogenesis that were observed by proteomics analysis in MCF7-fibroblast co-cultures.

The "mito-stemness" and "ribo-stemness" features of breast cancer cells resistant to hormone therapy, such as Tamoxifen, show that therapies involving one or more mitochondria-impairing agents could be used to specifically inhibit the treatment resistance the CSC population, paving the way for the identification of chemical strategies aimed at selectively targeting mitochondria in CSCs. The Mito-Signature described above may be used as in methods for predicting endocrine treatment therapy resistance and/or failure, overcoming endocrine treatment therapy resistance, and treating breast cancer (among others). The expression of each protein in the Mito-Signature in a sample of epithelial cancer tissue, and a sample of non-cancerous or normal cancer tissue, may be assessed. Over-expression of HSPD1, VDAC2, and CPT1A, in the cancer sample is prognostic of a risk of treatment failure, and indicates treatment with a mitochondrial inhibitor. It should be appreciated that the Mito-Signature described above may be used in combination with various therapeutic agents, for reducing and/or eliminating endocrine resistance, tumor recurrence, and metastasis, and thus for treating breast cancer.

Mitochondrial inhibition is an effective strategy for inhibiting cancer recurrence and metastasis, and for eradicating cancer cells and CSCs in particular. A number of categories of mitochondrial inhibitors may be used in connection with the present approach.

A first category of such therapeutics are mitoriboscins, as described in U.S. Pat. No. 10,512,618, issued Dec. 24, 2019 and incorporated by reference in its entirety. A second category of therapeutics include combination therapies involving oxidative metabolism inhibitors and glycolytic metabolism inhibitors. International Application No. PCT/US2018/028587, filed Apr. 20, 2018 and published as WO 2018/195434-A1, is incorporated by reference in its entirety. Some therapies may involve a triple combination having a first antibiotic inhibiting the large mitochondrial ribosome (such as, for example, members of the erythromycin family), a second antibiotic inhibiting the small mitochondrial ribosome (such as, for example, members of the tetracycline family), administered with a pro-oxidant or an agent inducing mitochondrial oxidative stress (e.g., low concentrations of Vitamin C, radiation therapy, among other examples). International Application No. PCT/US2018/028587, filed Dec. 16, 2019, incorporated by reference in its entirety, describes further examples.

A third category of mitochondrial biogenesis inhibitors, antimitoscins, is described in International Patent Application PCT/US2018/033466, filed May 18, 2018, and incorporated by reference in its entirety. A fourth category of mitochondria biogenesis inhibitors are mitoketoscins, non-carcinogenic compounds that bind to at least one of ACAT1/2 and OXCT1/2 and inhibit mitochondrial ATP production. These compounds are described more fully in International Application PCT/US2018/039354, filed Jun. 25, 2018, incorporated by reference in its entirety. Mitoflavoscins and mitoflavins are a fifth category of mitochondrial biogenesis inhibitors that may be used under the present approach. These compounds are described more fully in International Patent Application PCT/US2018/057093, filed Oct. 23, 2018 and incorporated by reference in its entirety. Mitoflavoscins are compounds that bind to flavin-containing enzymes and inhibit mitochondrial ATP production. Diphenyleneiodonium chloride (DPI) is an example of a mitoflavoscin. A sixth category of mitochondria biogenesis inhibitors are TPP-derivative compounds that show not only a strong preference for uptake in cancer cells (bulk cancer cells, cancer stem cells, and energetic cancer stem cells), but also disrupt mitochondrial biogenesis in these cells. These TPP-derivative compounds are described more fully in International Patent Application PCT/US2018/062174, filed Nov. 21, 2018, which is incorporated by reference in its entirety.

Repurposcins are a seventh category of mitochondria biogenesis inhibitors that may be used in embodiments of the present approach. International Patent Application PCT/US2018/062956, filed Nov. 29, 2018 and incorporated by reference in its entirety, describes these compounds more fully. In some embodiments, the inhibitor compound may be a myristol derivative of 9-amino-Doxycycline. For example, the inhibitor compound may have the general formula:

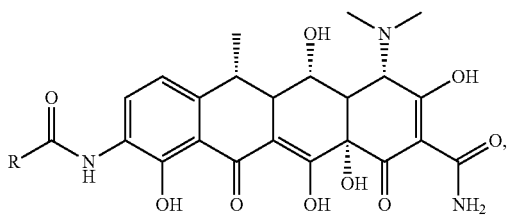

wherein R comprises a C4-C18 alkyl, or a pharmaceutically acceptable salt thereof. For example, in a preferred embodiment, R is 13. An eighth category of mitochondrial biogenesis inhibitors that may be used in the present approach are MDIVI-1 derivatives, as described in International Patent Application PCT/US2018/066247, filed Dec. 18, 2018 and incorporated by reference in its entirety. Mitochondrial division inhibitor-1 (mDIVI-1) is a small molecule that selectively and reversibly inhibits DRP1. It should be appreciated that other mitochondrial inhibitors may be used, without departing from the present approach.

The following paragraphs describe the materials and methods used in the foregoing discussion. Cell cultures: All cell culture experiments were carried out using human foreskin fibroblasts immortalized with the human telomerase reverse transcriptase (hTERTBJ1 cells) and human MCF7 breast cancer cells. hTERT-BJ1 fibroblasts and MCF7 cells were purchased from ATCC and maintained in complete media: DMEM (D6546, Sigma) supplemented with 10% fetal bovine serum (F7524, Sigma), 100 units/ml of penicillin, 100 μg/ml, streptomycin (P0781, Sigma) and 1% Glutamax (#35050087, Life Technologies). For all experiments, cells were incubated at 37° C. in a humidified atmosphere containing 5% CO2.

Co-culture versus mixed cell populations: Two million MCF7 cells were co-cultured in a regular 15 cm dish with two million hTERT-BJ1 fibroblasts, seeded in a 1:1 ratio. Likewise, the same number of either MCF7 cells or hTERT-BJ1 fibroblasts was seeded separately in 15 cm dishes as mono-cultures. After 72 h of cell culture cells were lysed in RIPA lysis buffer (R0278, Sigma) containing proteinase inhibitors (05 892 970 001, Roche) and kept at 4° C. for 20 minutes with rotation. Lysates were cleared by centrifugation for 10 minutes at 10,000×g and supernatants were collected. The protein concentration of the lysates was determined by using the BCA protein assay kit (23225, Pierce). Briefly, four μg of MCF7-hTERT-BJ1 co-culture lysate or two μg of hTERT-BJ1 monoculture lysate mixed with 2 μg of MCF7 monoculture protein lysate (4 μg of protein in total) were submitted to the CRUK Proteomics Core Facility, for label-free proteomic analysis.

For Label-free proteomics analysis, the following chemicals and sample preparation were used: Formic acid, trifluoroacetic acid, ammonium formate (10 M), ammonium bicarbonate TCEP (Tris (2-carboxyethyl)phosphine hydrochloride), MMTS (Methyl methanethiosulfonate) and trypsin were all obtained from Sigma. HPLC gradient grade acetonitrile was obtained from Fisher Scientific. Protein digestion occurred as follows: Lysate samples were thawed to room temperature and their concentrations equalised to 1 μg/μL (50 μL volume) with RIPA buffer, and further processed for trypsin digestion by sequential reduction of disulphide bonds with TCEP and alkylation with MMTS. Briefly, 1 μL benzonase (Novagen) was added to the 50 μL aliquot and placed on ice for 15 minutes. The sample was then taken to dryness using a SpeedVac, and resuspended in 22.5 μL trypsin reaction buffer (40 mM ammonium bicarbonate and 9% acetonitrile). One μL of 50 mM TCEP solution was added to each sample, mixed briefly and placed on a heater block at 60° C. for 60 minutes. After cooling to room temperature, 0.5 μL of 200 mM MMTS solution was added to each sample and allowed to react for 15 minutes. Trypsin was added in two waves to ensure efficient digestion of the sample. Firstly, 20 μg of sequencing grade trypsin was resuspended in 1800 μL of trypsin reaction buffer; 225 μL of this solution were added to each sample for digestion, and the reactions were left at 37° C. overnight with shaking (600 rpm). The following morning, a further aliquot of trypsin was added. Two ml of trypsin reaction buffer was added to 20 μL of sequencing grade trypsin; 250 μL of this solution were added to each of the digest samples from overnight, and the reactions were left at 37° C. for 4 hours with shaking (600 rpm). Thirty-five μL 10% formic acid were added to the 500 μL digest sample (0.7% final concentration of formic acid) to stop the digestion. The digested solution was diluted in 7.5 mL of acetonitrile containing 0.3% formic acid.

For HILIC solid phase extraction (SPE) of peptides: PolyhydroxyethylA SPE 12 μm, 300 A, 300 mg cartridges (obtained from PolyLC) were used for the HILIC procedure. Prior to use, cartridges required an overnight soak in 50 mM formic acid followed by rinsing with water the following day. Cartridges were preconditioned with 2 mL of Buffer A (90% acetonitrile, 5 mM ammonium formate, pH 2.7) followed by 2 mL of Buffer B (5 mM ammonium formate, pH 2.7) and finally re-equilibrated with 10 mL Buffer A. The diluted samples were loaded onto the cartridges and washed with a further 10 mL Buffer A. Finally, peptides were eluted in 1 mL Buffer C (9 parts Buffer B plus 1 part Buffer A) and the samples dried on a Speedvac to remove organic solvent prior to LCMS/MS analysis.

For LC-MS/MS analysis: Lyophilised digests were resuspended in 50 μL of 0.1% TFA to give an approximate concentration of 1 μg/μL. One μL injection volumes were used throughout resulting in an on-column peptide loading of approximately 1 μg per injection. Analysis was performed in quintuplicate for each sample. All LC-MS/MS analyses were performed on an LTQ Orbitrap XL mass spectrometer coupled to an Ultimate 3000 RSLCnano system (Thermo Scientific). One μL injection volumes were used throughout and samples loaded directly onto the analytical column, PepMap RSLC C18, 2 μm×75 μm id×50 cm (Thermo Scientific). The composition (v/v) of LC buffers were as follows; Buffer A—99.9% water plus 0.1% formic acid and Buffer B—80% acetonitrile, 19.9% water and 0.1% formic acid. Peptides were loaded directly onto the column at a flow rate of 400 nl/min with an initial mobile phase composition of 1% B. The organic strength was increased linearly from 1% to 22.5% B over 22.5 minutes again at 400 nl/min, followed by an increase to 24.8% B over the next 2.6 minutes with a concomitant reduction in flow rate to 300 nl/min, and to 39% B over a further 14 minutes. A further increase to 60% B over the next 5 minutes was followed by a ramp to 95% B over 2.5 minutes where it was held for a further 2 minutes. The column was then allowed to re-equilibrate to 1% B for a total analysis time of 74 minutes. The mass spectrometer was instructed to perform data dependent acquisition on the top six precursor ions, which were measured in the Orbitrap FTMS detector over the mass range 370-1200 m/z, at a nominal resolution of 60,000. MS/MS spectra were acquired in the ion trap under CID conditions with normalized collision energy of 35, isolation width of 3 Th, Q value of 0.25 and 30 ms activation time. Gasphase fractionation was performed on the five replicate injections such that MS/MS data was collected for precursor ion range 370-494 m/z Injection 1, 494-595 m/z Injection 2, 595-685 m/z Injection 3, 685-817 m/z Injection 4 and 817-1200 m/z Injection 5.

Statistical analysis was performed as follows: Xcalibur raw data files acquired on the LTQ-Orbitrap XL were directly imported into Progenesis LCMS software (Waters Corp) for peak detection and alignment. Data were analysed using the Mascot search engine. Five replicates were analysed for each sample type. Statistical analyses were performed using ANOVA and only fold-changes in proteins with a p-value less than 0.05 were considered significant. Proteomics and statistical analyses were carried out on a fee-for-service basis by Dr. Duncan Smith and his colleagues, at the Proteomics Core Facility at the *Cancer Research UK* Manchester Institute, University of Manchester.

Ingenuity pathway analyses were performed as follows: Pathway and function analyses were generated using Ingenuity Pathway Analysis (IPA) (Ingenuity systems, http://www.ingenuity.com), which assists with proteomics data interpretation via grouping differentially expressed genes or proteins into known functions and pathways. Pathways with a z score>1.9 were considered as significantly activated, and pathways with a z score<−1.9 were considered as significantly inhibited.

Validation with transcriptional profiling of breast cancer patient samples: To directly establish the clinical relevance of the proteomics analysis of MCF7-fibroblast co-cultures, the publically-available transcriptional profiles of epithelial breast cancer cells and adjacent tumor stromal cells that were physically separated by laser-capture microdissection (from N=28 human breast cancer patients) were re-analyzed.

Validation with Kaplan-Meier (K-M) analyses of breast cancer patient samples: The Kaplan-Meier analysis of mitochondrial gene transcripts used an open-access online survival analysis tool to interrogate publically available microarray data from up to 3,455 breast cancer patients. This allowed for assessing their prognostic value. For this purpose, data from ER(+) patients that were LN(+) at diagnosis and were of the luminal A sub-type, that were primarily treated with Tamoxifen and not other chemotherapy (N=152 patients), were used. In this group, 100% the patients received some form of hormonal therapy and ~95% of them received Tamoxifen. Biased and outlier array data were excluded from the analysis. This allowed for identifying mitochondrial gene transcripts, with significant prognostic value. Hazard-ratios were calculated, at the best auto-selected cut-off, and p-values were calculated using the logrank test and plotted in R. K-M curves were also generated online using the K-M-plotter (as high-resolution TIFF files), using univariate analysis:

http://kmplot.com/analysis/index.php?p=service&cancer=breast

This allowed the in silico validation of these mitochondrial biomarker candidates. The multi-gene classifier function of the program was used to test the prognostic value of short mitochondrial gene signatures, using the mean expression of the selected probes.

Validation via drug treatment of fluorescently-labeled MCF7-fibroblast co-cultures: hTERT-BJ1-RFP cells and MCF7-GFP cells were first generated by stable transduction with lenti-viral vectors. Then, these cells were plated into clear flat bottom 96-well black microplates (Corning; CLS3603). Mono-cultures were generated by plating either hTERT-BJ1-RFP (8,000 cells/well) or MCF7-GFP cells (8,000 cells/well). In parallel, co-cultures were generated by co-plating hTERT-BJ1-RFP (6,000 cells/well) with MCF7-GFP (2,000 cells/well). The next day, the plates were treated with either Doxycycline or Azithromycin (or vehicle controls) and were incubated for 72 hours at 37° C. The cell culture plates were then read with a plate-reader at 545/590 nm (for RFP) and at 490/510 nm (for GFP). Background readings were subtracted from the fluorescent signal and data were then normalized to controls.

The terminology used in the description of embodiments of the present approach is for the purpose of describing particular embodiments only and is not intended to be limiting. As used in the description and the appended claims, the singular forms "a," "an" and "the" are intended to include the plural forms as well, unless the context clearly indicates otherwise. The present approach encompasses numerous alternatives, modifications, and equivalents as will become apparent from consideration of the following detailed description.

It will be understood that although the terms "first," "second," "third," "a)," "b)," and "c)," etc. may be used herein to describe various elements of the present approach, and the claims should not be limited by these terms. These terms are only used to distinguish one element of the present approach from another. Thus, a first element discussed below could be termed an element aspect, and similarly, a third without departing from the teachings of the present approach. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. All publications, patent applications, patents and other references mentioned herein are incorporated by reference in their entirety. In case of a conflict in terminology, the present specification is controlling.

Also, as used herein, "and/or" refers to and encompasses any and all possible combinations of one or more of the associated listed items, as well as the lack of combinations when interpreted in the alternative ("or").

Unless the context indicates otherwise, it is specifically intended that the various features of the present approach described herein can be used in any combination. Moreover, the present approach also contemplates that in some embodiments, any feature or combination of features described with respect to demonstrative embodiments can be excluded or omitted.

As used herein, the transitional phrase "consisting essentially of" (and grammatical variants) is to be interpreted as encompassing the recited materials or steps "and those that do not materially affect the basic and novel characteristic(s)" of the claim. Thus, the term "consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measurable value may include any other range and/or individual value therein.

Having thus described certain embodiments of the present approach, it is to be understood that the scope of the appended claims is not to be limited by particular details set forth in the above description as many apparent variations thereof are possible without departing from the spirit or scope thereof as hereinafter claimed.

What is claimed is:

1. A method for identifying and treating endocrine therapy resistance in a cancer, the method comprising:
    obtaining a biological epithelial sample of a cancer;
    determining, or having determined, the level of each biomarker in a Mito-Signature comprising HSPD1, VDAC2, and CPT1A, in the biological sample;
    comparing the determined level to a threshold level of adjacent stroma for each biomarker in the Mito-Signature; and
    administering a pharmaceutically effective amount of a mitochondrial biogenesis inhibitor to the endocrine therapy resistant cancer indicated by a characteristic that the determined levels of at least two of the HSPD1, VDAC2, and CPT1A biomarkers in the Mito-Signature exceeds the threshold level.

2. The method of claim 1, wherein the method comprises determining the threshold level for each biomarker in the Mito-Signature using an adjacent non-cancerous epithelial sample.

3. The method of claim 1, wherein the cancer comprises breast cancer.

4. The method of claim 1, wherein the pharmaceutically effective amount of the mitochondrial biogenesis inhibitor is administered to the endocrine therapy resistant cancer indicated by a characteristic that the determined levels of each of the HSPD1, VDAC2, and CPT1A biomarkers in the Mito-Signature exceeds the threshold level.

5. The method of claim 1, wherein the mitochondrial biogenesis inhibitor comprises one of doxycycline and azithromycin.

6. The method of claim 1, wherein the mitochondrial biogenesis inhibitor comprises a compound having the general formula:

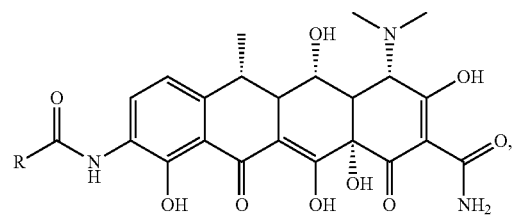

wherein R comprises a C4-C18 alkyl, or a pharmaceutically acceptable salt thereof.

7. The method of claim 1, wherein the at least one mitochondrial biogenesis inhibitor comprises at least one of a mitoriboscin, the combination of an oxidative metabolism inhibitor and a glycolytic metabolism inhibitor, a repurposcin, an antimitoscin, a mitoketoscin, a mitoflavoscin, a mitoflavin, a TPP structural derivative, and a Mitochondrial division inhibitor-1 (MDIVI-1) structural derivative.

8. The method of claim 7, wherein the at least one mitochondrial biogenesis inhibitor comprises a mitoriboscin selected from the group consisting of:

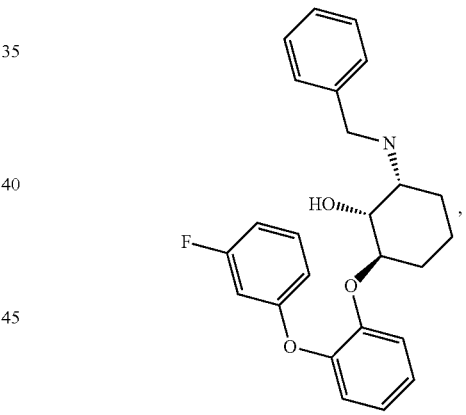

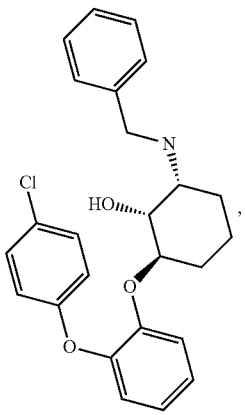

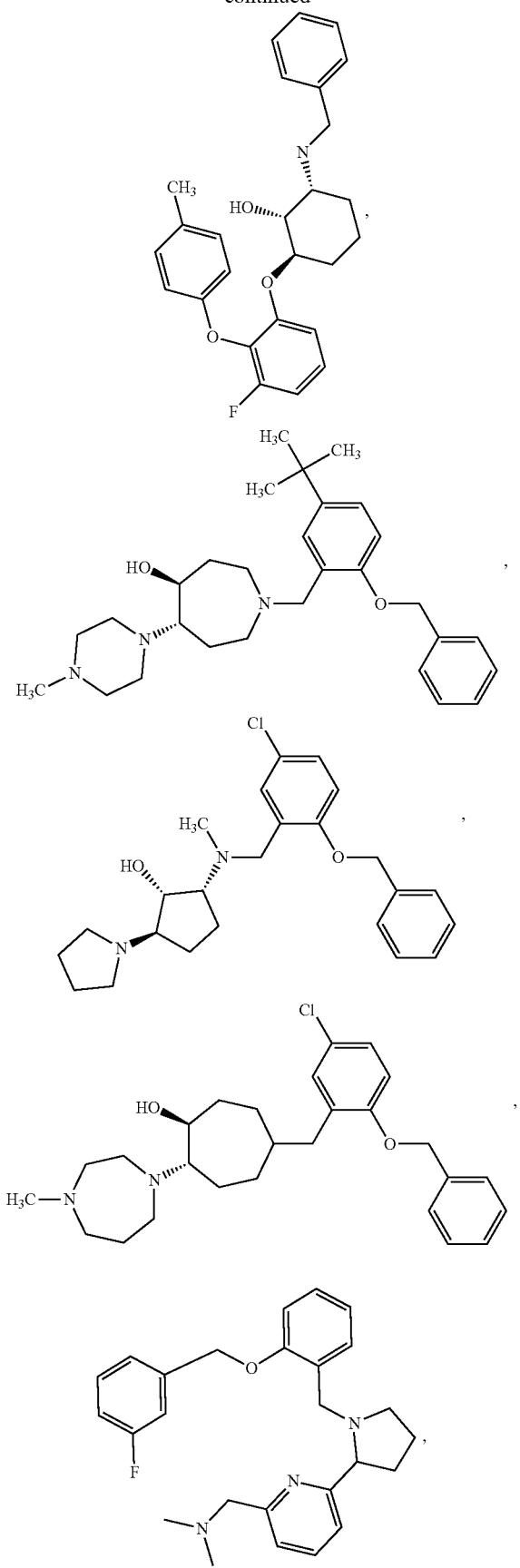

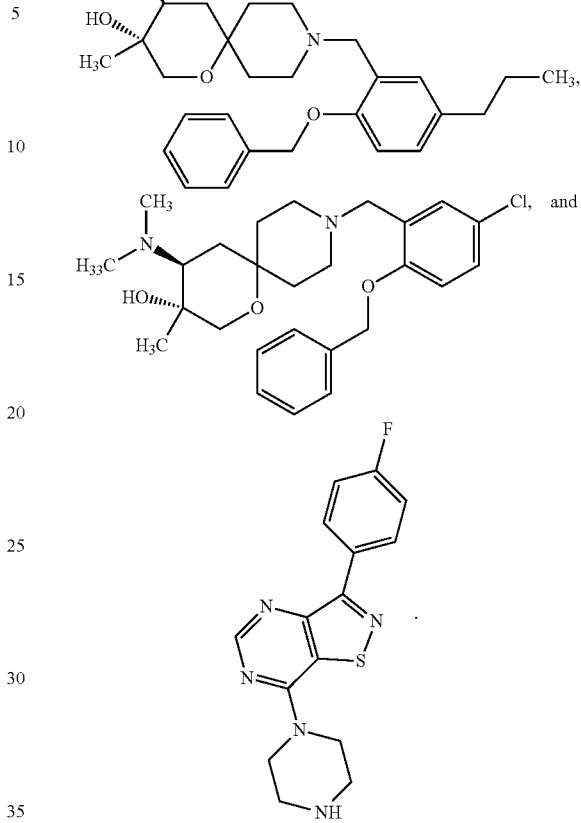

9. The method of claim 7, wherein the at least one mitochondrial biogenesis inhibitor comprises the combination of:
   an oxidative metabolism inhibitor selected from the group comprising: tetracycline, doxycycline, tigecycline, minocycline, chlortetracycline, oxytetracycline, demeclocycline, lymecycline, meclocycline, methacycline, rolitetracycline, chlortetracycline, omadacycline, sarecycline, erythromycin, azithromycin, and clarithromycin; and
   a glycolytic metabolism inhibitor selected from the group comprising of: a glycolysis inhibitor, an OXPHOS inhibitor, and an autophagy inhibitor.

10. The method of claim 9, wherein the glycolytic metabolism inhibitor is at least one of the following:
    a glycolysis inhibitor comprising one of 2-deoxy-glucose, ascorbic acid, and stiripentol;
    an OXPHOS inhibitor comprising one of atoravaquone, irinotecan, sorafenib, niclosamide, and berberine chloride; and
    an autophagy inhibitor comprising chloroquine.

11. The method of claim 9, wherein the mitochondrial biogenesis inhibitor comprises a combination of doxycycline, azithromycin, and ascorbic acid.

12. The method of claim 7, wherein the at least one mitochondrial biogenesis inhibitor comprises an antimitoscin selected from the group consisting of:
    an antibiotic comprising at least one of: a member of the tetracycline family, a member of the erthyromycin family, chloramphenicol, pyrvinium pamoate, atovaquone, and bedaquiline;

wherein the antibiotic has been chemically modified with at least one mitochondrial targeting signal.

13. The method of claim 11, wherein the mitochondrial targeting signal comprises at least one of palmitic acid, stearic acid, myristic acid, oleic acid, a short-chain fatty acid, a medium-chain fatty acids a lipophilic cation, tri-phenyl-phosphonium, a structural derivative of tri-phenyl-phosphonium, guanidinium, a guanidinium derivative, and 10-N-nonyl acridine orange.

14. The method of claim 7, wherein the at least one mitochondrial biogenesis inhibitor comprises a mitoketoscin having a structural formula selected from the group consisting of:

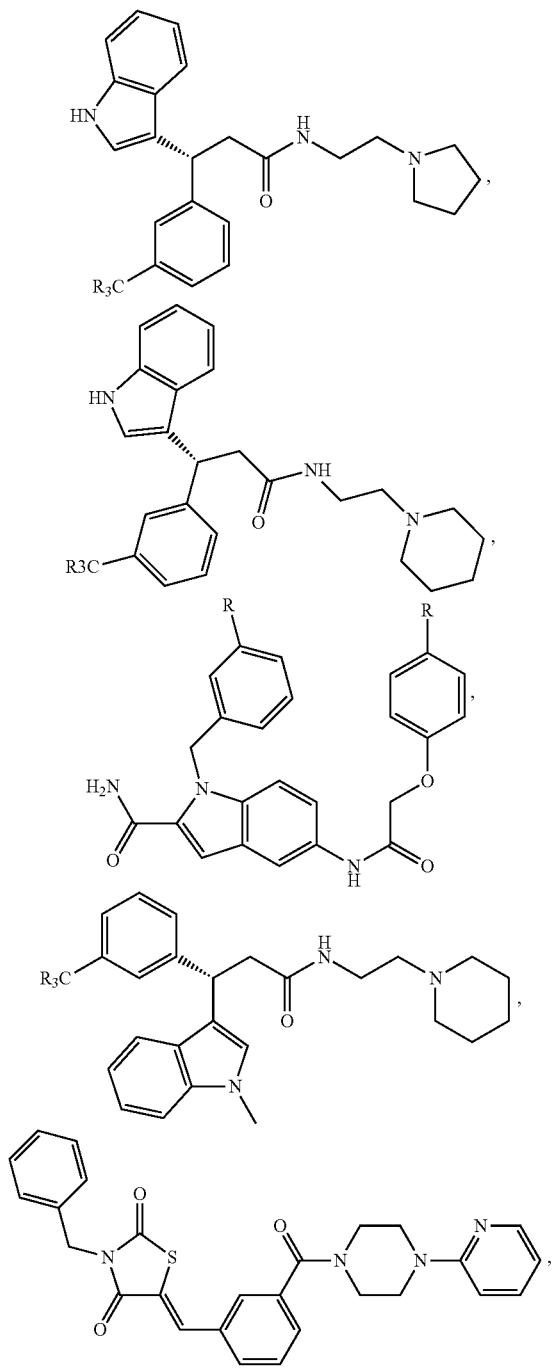

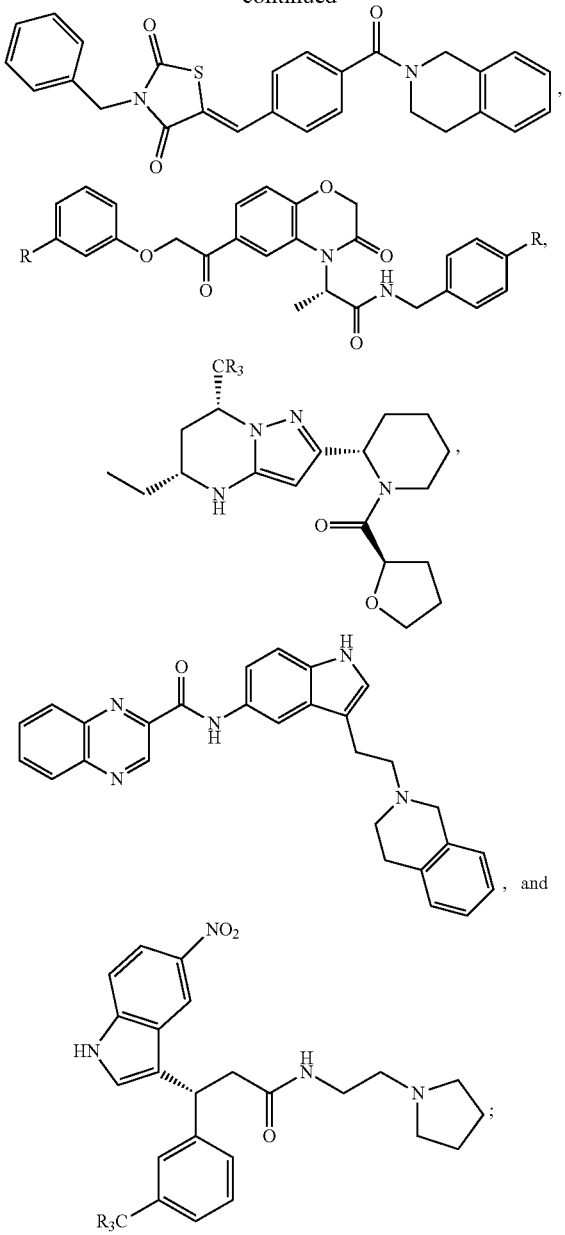

or a pharmaceutically acceptable salt thereof, wherein each R is the same or different, and is selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives.

15. The method of claim 7, wherein the at least one mitochondrial biogenesis inhibitor comprises at least one of a mitoflavoscin and a mitoflavin, wherein the mitoflavoscin comprises diphenyleneiodonium chloride, and the mitoflavin is selected from the group consisting of roseoflavin, lumichrome, alloxazine, lumiflavine, 1,5-dihydroriboflavin, and 1,5-dihydroflavin.

16. The method of claim 14, wherein the mitochondrial biogenesis inhibitor further comprises at least one chemical modification with a mitochondrial targeting signal selected from the group consisting of palmitic acid, stearic acid, myristic acid, oleic acid, a short-chain fatty acid, a medium-chain fatty acid, a lipophilic cation, tri-phenyl-phosphonium, a structural derivative of tri-phenyl-phosphonium, guanidinium, a guanidinium structural derivative, and 10-N-nonyl acridine orange.

17. The method of claim 7, wherein the at least one mitochondrial biogenesis inhibitor comprises a TPP-derivative selected from the group consisting of 2-butene-1,4-bis-TPP; 2-chlorobenzyl-TPP; 3-methylbenzyl-TPP; 2,4-dichlorobenzyl-TPP; 1-naphthylmethyl-TPP; and p-xylylenebis-TPP.

18. The method of claim 17, wherein the mitochondrial biogenesis inhibitor further comprises at least one chemical modification with a mitochondrial targeting signal selected from the group consisting of palmitic acid, stearic acid, myristic acid, oleic acid, a short-chain fatty acid, a medium-chain fatty acid, a lipophilic cation, tri-phenyl-phosphonium, a structural derivative of tri-phenyl-phosphonium, guanidinium, a guanidinium structural derivative, and 10-N-nonyl acridine orange.

19. The method of claim 7, wherein the at least one mitochondrial biogenesis inhibitor comprises an MDIVI-1 structural derivative having the general formula:

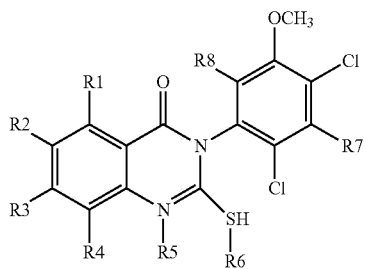

or a pharmaceutically acceptable salt thereof, wherein each of R1 through R8 is selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, benzoic acid-based derivatives, and a mitochondrial targeting signal.

20. The method of claim 19, wherein the MDIVI-1 structural derivative comprises at least one mitochondrial targeting signal selected from the group consisting of: palmitic acid; stearic acid; myristic acid; oleic acid; a short-chain fatty acid; a medium-chain fatty acid; a lipophilic cation; tri-phenyl-phosphonium (TPP); a structural TPP-derivative; 2-butene-1,4-bis-TPP; 2-chlorobenzyl-TPP; 3-methylbenzyl-TPP; 2,4-dichlorobenzyl-TPP; 1-naphthylmethyl-TPP; p-xylylenebis-TPP; and 10-N-nonyl acridine orange.

21. The method of claim 7, wherein the at least one mitochondrial biogenesis inhibitor comprises a repurposcin, comprising:
at least one compound selected from the group comprising:
berberine chloride, quercetin, niclosamide, acriflavinium hydrochloride, sorafenib, emetine dihydrochloride, dactinomycin, plicamycin, suloctidil, teniposide, pentamidine isethionate, daunorubicin, thioguanine, amsacrine, phenformin hydrochloride, irinotecan hydrochloride, mitomycin, hydroxyprogesterone caproate, cyclosporine, lanatoside c, mercaptopurine, quinacrine hydrochloride, fenofibrate, neomycin, puromycin, rapamycin, everolimus, G418, trovafloxacin, levofloxacin, avocatin B, clarithromycin, ciprofloxacin, spiramycin, telithromycin, norfloxacin, moxifloxacin, ofloxacin, minocycline, tetracycline, demethylchlortetracycline, a member of the tetracycline family, a member the erthyromycin family, clindamycin, metronidazole, linezolid, mupirocin, vancomycin, clindamycin, cephalosporin, ciprofolxacin, streptomycin, amoxicillin, and azelaic acid;
wherein the at least one compound is chemically modified with at least one mitochondrial targeting signal selected from the group comprising:
palmitic acid; stearic acid; myristic acid; oleic acid; a short-chain fatty acid; a medium-chain fatty acid; a lipophilic cation; tri-phenyl-phosphonium (TPP); 2-butene-1,4-bis-TPP; 2-chlorobenzyl-TPP; 3-methylbenzyl-TPP; 2,4-dichlorobenzyl-TPP; 1-naphthylmethyl-TPP; p-xylylenebis-TPP; and 10-N-nonyl acridine orange.

22. A method for identifying and treating endocrine therapy resistance in breast cancer, the method comprising:
obtaining a biological sample of a breast cancer;
determining, or having determined, the level of each biomarker in a combination of mitochondrial biomarkers prognostic of endocrine therapy resistance in the biological sample, the mitochondrial biomarkers comprising HSPD1, VDAC2, and CPT1A;
comparing the determined level to a threshold level of adjacent stroma for each of the HSPD1, VDAC2, and CPT1A mitochondrial biomarkers; and
administering a pharmaceutically effective amount of a mitochondrial biogenesis inhibitor to the endocrine therapy resistant breast cancer indicated by a characteristic that the determined levels of each of the HSPD1, VDAC2, and CPT1A mitochondrial biomarkers exceeds the threshold level,
wherein the at least one mitochondrial biogenesis inhibitor is selected from the group consisting of: tetracycline, doxycycline, tigecycline, minocycline, eyrthromycin, azithromycin, clarithromycin, pyrvinium pamoate, atovaquone, bedaquiline, irinotecan, sorafenib, niclosamide, berberine, stiripentol, chloroquine, etomoxir, perhexiline, a mitoriboscin, a mitoketoscin, a mitoflavoscin, a mitoflavin, a TPP-derivative, an mDIVI-1 structural derivative, caffeic acid phenyl ester, an antimitoscin, and a repurposcin.

23. A method for increasing the effectiveness of an endocrine therapy on breast cancer, the method comprising:
obtaining a biological sample of a breast cancer;
determining, or having determined, the level of each mitochondrial biomarker in a combination of biomarkers prognostic of endocrine therapy resistance in the biological sample, the combination of biomarkers comprising HSPD1, VDAC2, and CPT1A;
comparing the determined level to a threshold level of adjacent stroma for each of the HSPD1, VDAC2, and CPT1A mitochondrial biomarkers; and
administering, in conjunction with an endocrine therapy, a pharmaceutically effective amount of a mitochondrial biogenesis inhibitor to the breast cancer indicated by a characteristic that the determined level of each of the HSPD1, VDAC2, and CPT1A mitochondrial biomarkers exceeds the threshold level.

24. The method of claim 23, wherein the endocrine therapy comprises at least one of Tamoxifen and Fulvestrant.

25. The method of claim 23, wherein the mitochondrial biogenesis inhibitor comprises one of tetracycline, doxycycline, tigecycline, minocycline, eyrthromycin, azithromycin, clarithromycin, pyrvinium pamoate, atovaquone, bedaquiline, irinotecan, sorafenib, niclosamide, stiripentol, chloroquine, etomoxir, perhexiline, a mitoriboscin, a mitoketoscin, a mitoflavoscin, a mitoflavin, a TPP structural derivative, an mDIVI-1 structural derivative, caffeic acid phenyl ester, an antimitoscin, and a repurposcin.

26. A method of increasing the effectiveness of an endocrine therapy, the method comprising administering a pharmaceutically effective amount of a mitochondrial biogenesis inhibitor to a cancer having an up-regulated HSPD1, VDAC2, and CPT1A compared to adjacent stroma.

27. The method of claim 26 wherein the mitochondrial biogenesis inhibitor comprises at least one of tetracycline, doxycycline, tigecycline, minocycline, eyrthromycin, azithromycin, clarithromycin, pyrvinium pamoate, atovaquone, bedaquiline, irinotecan, sorafenib, niclosamide, berberine, stiripentol, chloroquine, etomoxir, perhexiline, a mitoriboscin, a mitoketoscin, a mitoflavoscin, a mitoflavin, a TPP structural derivative, an mDIVI-1 structural derivative, caffeic acid phenyl ester, an antimitoscin, and a repurposcin.

28. The method of claim 26, wherein the endocrine therapy comprises Tamoxifen and Fulvestrant.

29. The method of claim 26, further comprising, after administering the mitochondrial biogenesis inhibitor, administering the endocrine therapy.

30. The method of claim 26, further comprising, at the same time as administering the at least one mitochondrial biogenesis inhibitor, administering the endocrine therapy.

* * * * *